(12) United States Patent
Ganey et al.

(10) Patent No.: US 12,226,532 B2
(45) Date of Patent: *Feb. 18, 2025

(54) COATED BIOLOGICAL COMPOSITION

(71) Applicant: Vivex Biologics Group, Inc., Atlanta, GA (US)

(72) Inventors: Timothy Ganey, Tampa, FL (US); Tracy Scott Anderson, Atlanta, GA (US)

(73) Assignee: VIVEX BIOLOGICS GROUP, INC., Atlanta, GA (US)

( * ) Notice: Subject to any disclaimer, the term of this patent is extended or adjusted under 35 U.S.C. 154(b) by 321 days.

This patent is subject to a terminal disclaimer.

(21) Appl. No.: 17/072,625

(22) Filed: Oct. 16, 2020

(65) Prior Publication Data
US 2021/0030688 A1 Feb. 4, 2021

Related U.S. Application Data

(60) Division of application No. 15/898,558, filed on Feb. 17, 2018, which is a continuation-in-part of application No. 15/837,694, filed on Dec. 11, 2017, now Pat. No. 11,160,904, which is a continuation-in-part of application No. 15/591,513, filed on May 10, 2017, now Pat. No. 10,513,690, and a continuation-in-part of application No. 15/590,444, filed on May 9, 2017, now abandoned, which is a continuation-in-part of application No. 15/590,475, filed on May 9, 2017, now Pat. No. 10,760,058, said application No. 15/898,558 is a continuation-in-part of application No. 15/591,513, filed on May 10, 2017, now Pat. No. 10,513,690, which is a division of application No. 14/683,221, filed on Apr. 10, 2015, now Pat. No. 9,675,643, said application No. 15/898,558 is a continuation-in-part of application No. 15/590,444, filed on May 9, 2017, now abandoned, which is a division of application No. 14/682,523, filed on Apr. 9, 2015, now Pat. No. 9,687,511, said application No. 15/898,558 is a continuation-in-part of application No. 15/590,475, filed on May 9, 2017, now Pat. No. 10,760,058, which is a division of application No. 14/682,523, filed on Apr. 9, 2015, now Pat. No. 9,687,511.

(60) Provisional application No. 62/129,351, filed on Mar. 6, 2015, provisional application No. 62/129,337, filed on Mar. 6, 2015.

(51) Int. Cl.
| | |
|---|---|
| *A61K 35/12* | (2015.01) |
| *A61K 9/50* | (2006.01) |
| *A61K 9/51* | (2006.01) |
| *A61L 27/36* | (2006.01) |
| *A61L 27/38* | (2006.01) |
| *C12N 5/0775* | (2010.01) |
| *C07C 31/22* | (2006.01) |
| *C07C 317/04* | (2006.01) |
| *C07H 3/04* | (2006.01) |
| *C09D 177/04* | (2006.01) |

(52) U.S. Cl.
CPC .......... *A61K 9/5031* (2013.01); *A61K 9/5123* (2013.01); *A61L 27/3608* (2013.01); *A61L 27/3804* (2013.01); *C12N 5/0663* (2013.01); *A61L 2430/38* (2013.01); *C07C 31/225* (2013.01); *C07C 317/04* (2013.01); *C07H 3/04* (2013.01); *C09D 177/04* (2013.01)

(58) Field of Classification Search
None
See application file for complete search history.

(56) References Cited

U.S. PATENT DOCUMENTS

| | | |
|---|---|---|
| 2,622,027 A | 12/1952 | Torr |
| 5,837,539 A | 11/1998 | Caplan et al. |
| 9,192,695 B2 | 11/2015 | Shi |

(Continued)

FOREIGN PATENT DOCUMENTS

| | | |
|---|---|---|
| WO | 2014159662 | 10/2014 |
| WO | 2015016761 | 2/2015 |

OTHER PUBLICATIONS

Merriam-Webster, Extant definition, retreived from the internet 03242023: https://www.merriam-webster.com/dictionary/extant (Year : 2023).*

(Continued)

*Primary Examiner* — Evelyn Y Pyla
(74) *Attorney, Agent, or Firm* — Kilpatrick Townsend & Stockton LLP

(57) ABSTRACT

A coated biological composition has a mixture of biologic material and a volume of a liquid protectant. The mixture of biologic material has non-whole cellular components or whole cells or combinations of the non-whole cellular components and whole cells, wherein the mixture is compatible with biologic function. The volume of a liquid protectant is intermixed with the mixture of biologic material, wherein the liquid protectant forms a coating externally enveloping each of the non-whole cellular components, if any, and each of the whole cells, if any, of the mixture of biologic material, to form the coated biological composition. The coated biological composition is frozen and thereafter thawed and then frozen a second time for storage or frozen at least once and thawed and stored under refrigeration above freezing, or frozen and thawed and then concentrated by drying, or while frozen without thawing lyophilized for ambient or room temperature storage.

43 Claims, 21 Drawing Sheets

(20 of 21 Drawing Sheet(s) Filed in Color)

(56) References Cited

U.S. PATENT DOCUMENTS

| | | |
|---|---|---|
| 9,603,355 B2 | 3/2017 | Matsumura et al. |
| 9,675,643 B2 | 6/2017 | Weston et al. |
| 9,687,511 B2 | 6/2017 | Weston et al. |
| 2003/0069639 A1 | 4/2003 | Sander |
| 2004/0097612 A1 | 5/2004 | Rosenberg et al. |
| 2005/0013872 A1 | 1/2005 | Freyman |
| 2007/0191963 A1 | 8/2007 | Winterbottom et al. |
| 2008/0014179 A1 | 1/2008 | Ferree |
| 2008/0268429 A1 | 10/2008 | Pietrzkowski |
| 2010/0105132 A1 | 4/2010 | Totey et al. |
| 2011/0172315 A1 | 7/2011 | Matsumura et al. |
| 2012/0053692 A1 | 3/2012 | Voor et al. |
| 2013/0059782 A1 | 3/2013 | Murat et al. |
| 2013/0071358 A1 | 3/2013 | Peterson |
| 2014/0065240 A1 | 3/2014 | Mitsialis |
| 2014/0212949 A1* | 7/2014 | Kim .................. C12Q 1/37 435/226 |
| 2015/0132266 A1 | 5/2015 | Schiller et al. |
| 2016/0015753 A1 | 1/2016 | Temple |
| 2016/0030639 A1 | 2/2016 | Shi |
| 2016/0256490 A1 | 9/2016 | Weston et al. |

OTHER PUBLICATIONS

Collins Dictionary, Metabolome definition, retrieved from the internet: https://www.collinsdictionary.com/us/dictionary/english/metabolome (Year: 2023).*

ATCC Thawing, Propagating and Cryopreserving Protocol for NCI-PBCF-CRL, A-375 Malignant melanoma cells, Sep. 12, 2013 (Year: 2013).*

Lorincz et al., Journal of Extracellular Vesicles, 2014, pp. 1-8 (Year: 2014).*

Linetsky et al., CellR4 2013; 1(3): e577, 15 pages (Year: 2013).*

Bone Structure and Function; ASBMR educational materials; https://depts.washington.edu/bonebio/ASBMRed/structure.html.

Cells and Organelles; http://biology.cld.uc.edu/courses/bio104/cells.htm.

Derivative definition; Merriam Webster; http://www.merriam-webster.com/dictionary/derivative.

E.Linetsky, N.Kenyon, H.Li, X.Xu and C.Ricordi; Increased Immunogenicity of Human Vertebral Body Marrow After Processing in Bovine Versus Human Serum Albumin; Elsevier Science Inc.; Transplantation Proceedings 29, 1960 (1997).

Matsumura, Kazuaki; Hyon, Suong-Hyu; Polampholytes as low toxic efficient cryoprotective agents with antifreeze protein properties; Biomaterials 30, 2009, 4842-4849.

Nottestad, Sheri Y.; Baumel, Julian J.; Kimmel, Donald B.; Recker, Robert R. and Heany, Robert P; The Proportion of Trabecular Bone in Human Vertebrae; Journal of Bone and Mineral Research, vol. 2, No. 3 1987.

Oryan et al; Bone regenerative medicine: classic options, novel strategies, and future directions, Journal of Orthopaedic Surgery and Research, 2014, vol. 9:18, pp. 1-27.

Brockbank et al., Advances in Biopreservation, 2006, pp. 157-196; retrieved from the internet; www.andrew.cmu.edu/user/yr25/TaylorPublications/MJTaylor108.pdf.

Liu et al., Nanoscale, 2017, vol. 9, pp. 4430-4438 (Year: 2017).

Nishimura et al Spine, 1998, vol. 23, Issue 14, pp. 1531-1538 (Year: 1998).

Matsumura et al., Journal of Biomaterials Science, Polymer Edition, 2013, vol. 24, No. 12, pp. 1484-1497 (Year: 2013).

Matsumura et al., Cell Transplantation, vol. 19, pp. 691-699, 2010 (Year: 2010).

Weston et al., BioDrugs (2019) 33: 137-158 (Year: 2019).

U.S. Appl. No. 15/590,444, "Final Office Action," Dec. 21, 2023, 15 pages.

U.S. Appl. No. 15/898,558, "Non-Final Office Action," Feb. 23, 2024, 26 pages.

Hiraki et al., "Use of ADME Studies to Confirm the Safety of E-polylysine as a Preservative in Food," Regulatory Toxicology and Pharmacology, vol. 37, No. 2, 2003, pp. 328-340.

Shi et al., "Antimicrobial, Antioxidant, and Antitumor Activity of Epsilon-poly-l-lysine and Citral, Alone or in Combination," Food & Nutrition Research, vol. 60, No. 31891, 2016, 8 pages.

Williams et al., "Mesenchymal Stem Cells: Biology, Pathophysiology, Translational Findings, and Therapeutic Implications for Cardiac Disease," Circulation Research, 2011, vol. 109, pp. 923-940.

U.S. Appl. No. 15/898,558, "Final Office Action", mailed Oct. 7, 2024, 28 pages.

* cited by examiner

Polyampholyte cryoprotectant  DMSO-based cryoprotectant

Exosome – Context and Illustration

Scientific Acceptance
- Human Biology is accountable to cell-cell exchange
- Cell lineages exchange genetic material with other cells
- Receiving cells adopt functions of donating cells.

COATED BIOLOGICAL COMPOSITION

RELATED APPLICATIONS

The present application is a division of co-pending application U.S. Ser. No. 15/898,558 filed on Feb. 17, 2018 which is a continuation in part of application U.S. Ser. No. 15/837,694 entitled, "Biological Composition In A Protectant Shroud And Methods" filed on Dec. 11, 2017 which is a continuation in part of U.S. Ser. No. 15/591,513 filed on May 10, 2017 now U.S. Pat. No. 10,513,690 and a continuation in part of U.S. Ser. No. 15/590,444 filed on May 9, 2017 and a continuation in part of U.S. Ser. No. 15/590,475 filed on May 9, 2017; and U.S. Ser. No. 15/898,558 is a continuation in part of U.S. Ser. No. 15/591,513 entitled, "Biologic Composition And Method Of Manufacture" filed on May 10, 2017 which is a division of U.S. Ser. No. 14/683,221 filed on Apr. 10, 2015 now U.S. Pat. No. 9,675,643 which claims priority to provisional 62/129,337 filed on Mar. 6, 2015; and U.S. Ser. No. 15/898,558 is a continuation in part of U.S. Ser. No. 15/590,444 entitled, "Acellular Biologic Composition And Method Of Manufacture" filed on May 9, 2017 which is a division of U.S. Ser. No. 14/682,523 filed on Apr. 9, 2015 now U.S. Pat. No. 9,687,511 which claims priority to provisionals U.S. 62/129,337 filed on Mar. 6, 2015 and U.S. Ser. No. 62/129,351 filed on Mar. 6, 2015; and U.S. Ser. No. 15/898,558 is a continuation in part of U.S. Ser. No. 15/590,475 entitled, "Acellular Biologic Composition And Method Of Manufacture" filed on May 9, 2017 now U.S. Pat. No. 10,760,058 which is a division of U.S. Ser. No. 14/682,523 filed on Apr. 9, 2015 now U.S. Pat. No. 9,687,511 which claims priority to provisionals U.S. 62/129,337 filed on Mar. 6, 2015 and U.S. 62/129,351 filed on Mar. 6, 2015.

TECHNICAL FIELD

This invention is a tissue regenerative biologic composition. More specifically, a composition at least in part formed from bone marrow and a method of manufacture and use of said composition with an acellular mixture.

BACKGROUND OF THE INVENTION

In the area of tissue regeneration or repair, the use of stem cell therapy has been widely touted.

Often, these inventions describe isolating the stem cells, purifying and culturally expanding mesenchymal stem cells. In U.S. Pat. No. 5,837,539, entitled "Monoclonal Antibodies For Human Mesenchymal Stem Cells", Arnold Caplan et al. reported that the cells are preferably culturally expanded, but suggest it is possible to use the stem cells without culture expansion. Caplan also describes a way to isolate stem cells.

A major technological hurdle to producing a safe allogeneic composition with viable cells has been the need to approach a fraction of risk approaching zero by removing all antigenic properties that lead to inflammation factors in a separation to yield only a certain stromal cell type. This has proven difficult in practice, as the in-process access degrades the quantity of viable cells that can be effectively harvested.

The present invention has yielded a biological composition that is safe and achieves favorable patient outcomes after direct implantation and does so in a method that allows a resultant mixture of biologic material to be recovered from human cadaver tissue such as bone marrow wherein the mixture unexpectedly exhibits evidence of viability independent of whole cells such as mesenchymal cells in the dose while sustaining a legacy or memory of the lineages from where the acellular biological composition came which retains the ability to support the emergence of new tissue forms including bone and other tissues. The mixture can include whole cells in combination with the acellular material or can be primarily whole cell based. The mixture is coated in a protectant suitable for direct implantation.

A particular challenge of cryoprotection is long term storage at sub-zero temperature, sustaining protection in transit, and validation of shelf life incumbent to assuring viability. Previous work assigned a critical role for successful allograft potency in cell viability, but the inventors of the present invention in more recent observations discovered that cell viability in and of itself may not fully constitute the effect of a cellular matrix in the transfer of potential for regenerative activity. In particular, less viable compositions are showing exceptional activity to comport gene activity, accentuate bone formation, and to vascularize tissue for rapid bone healing in clinical applications. Other work is showing that collected marrow exudate can be used to enhance inorganic matrix carriers particularly in the context of intended bone repair.

These observations had guided the inventors to additional considerations that attend potential for using a protectant covering onto cellular and cell fraction compositions in unique ways to observe a remarkable new composition that affords unique method of manufacture and usages as described hereinafter.

These and other benefits of the present invention and the method of preparing it are described hereinafter.

SUMMARY OF THE INVENTION

A coated biological composition has a mixture of biologic material and a volume of a liquid protectant. The mixture of biologic material has non-whole cellular components including vesicular components and active and inactive components of biological activity, cell fragments, cellular excretions, cellular derivatives, and extracellular components, or whole cells or combinations of the non-whole cellular components and whole cells, wherein the mixture is compatible with biologic function. The volume of a liquid protectant is intermixed with the mixture of biologic material, wherein the liquid protectant forms a coating externally enveloping each of the non-whole cellular components, if any, and each of the whole cells, if any, of the mixture of biologic material, to form the coated biological composition. The coated biological composition is frozen and thereafter thawed and then frozen a second time for storage or frozen at least once and thawed and stored under refrigeration above freezing, or frozen and thawed and then concentrated by drying, or while frozen without thawing lyophilized for ambient or room temperature storage.

In one embodiment, the thawed coated biological composition is concentrated by drying prior to being stored at room temperature to form a dried coated biological composition, wherein the coated biological composition is freeze dried or hypothermic dehydrated. The dried coated biological composition optionally can be micronized into particles of 1000 microns or less. In one embodiment, the dried coated biological composition can be micronized into particles of 400 microns or less.

Preferably, the dried coated biological composition has a moisture content of 5% or less, wherein an initial volume of the liquid protectant when reduced to a solid for drying or freeze-drying yields 5% or less of the initial volume.

The liquid protectant can be a polyampholyte protectant or polyampholyte cryoprotectant, or a glycerol based protectant, or dimethyl sulfoxide (DMSO) or glycols or trehalose or sucrose or dextrose.

In at least one embodiment, the dried coated biological composition when reconstituted in a liquid is suitable for direct implantation.

The coated biological composition further may include a volume of one of cartilage particles or nucleus pulposus particles or bone particles; the particles intermixed with the biological material and coated with the liquid protectant.

The biological composition can be used in conjunction with bone allograft or separately as a preparation that can be used to attend other combinations of blended bone, milled bone, shaped bone, micronized bone, powdered bone pastes, bone-tendon graft combinations, cartilage compositions that have been micronized, powdered, and enhanced with polyampholyte-enriched preservation that can be frozen, can be thawed and refrozen, or can be thawed and concentrated to enrich allograft compositions.

In specific applications, cellular based biomaterial that has been treated with a polyampholyte protectant may be combined in various embodiments that may comprise porous and non-porous materials designed to delay the kinetics of deployment, alter or manage specific biologic properties, and in conjunction with polymers, fleeces, and natural materials such as collagen, or meshes, or ceramics, in conjunction with allograft materials.

The combination of the polyampholyte, cryoprotected, and ambient temperature biologics is intended to impart release variations of systemic factors in both the cellular and solid components of the allograft, functionally shifting surface affinity, inter-graft fluid viscosity during resorption, radiopacity, bacteriocidicity, and reducing the need for the polyampholyte to functionally preserve biologic activity previously thought to be restricted to storage and maintenance only at sub-zero temperatures.

In one embodiment, a biological composition intermixed with a polyampholyte protectant for direct implantation has a mixture of biologic material and a volume of polyampholyte protectant. The mixture of biologic material has non-whole cellular components including vesicular components and active and inactive components of biological activity, cell fragments, cellular excretions, cellular derivatives, and extracellular components, or whole cells or combinations of the non-whole cellular components and whole cells, wherein the mixture is compatible with biologic function. The volume of polyampholyte protectant is intermixed with the mixture of biologic material, wherein the polyampholyte protectant is a liquid of a polyamine polymer compound of carboxylated poly-lysine and wherein the polyampholyte protectant forms a three-dimensional coating externally enveloping each of the non-whole cellular components, if any, and each of the whole cells, if any, of the mixture of biologic material.

The coating deters attachment to other cells or to other tissues for an undetermined time. The coating also buffers inflammation and further can retard or reduce premature differentiation of the whole cells of the mixture. The coating also sustains regenerative potential and biologic function of the mixture during preservation and implantation. The coating can be configured to be metabolized after implantation after a predetermined time, the predetermined time can be three or more days, the predetermined time can be six days. Alternatively, the coated biological composition can be configured to be metabolized in a much shorter time or a rapid burst, a separation of an open face of the bioavailability and it occurring in less than 3 days. The coating when enveloping a whole cell forms a spherical shell about each whole cell. Preferably, the polyampholyte protectant is a cryoprotectant.

The polyampholyte contains cells, non-whole cells, and various exosomal fractions that contribute to biologic activity. Placement of this material has been considered with allograft, and the allograft serves a function of using paracrine trajectory as a guide to cell differentiation and phenotypic synergy. To that point, clarification would suggest that a concentrated marrow-derived cell product would make bone when mixed with suitable bone carrier but would retain a potential to contribute to intervertebral disc regeneration if combined with disc, or to contribute to cartilage repair if mixed with cartilage allograft.

This application contends that an alternative method of preparing a biologically enhanced, clinically effective allograft can be defined where suitable allograft of various compositions and design can be used without prejudice to elaborate description as to size of graft, range of fiber, limitations of sizing via micronization, or other fractional claims to undermine the whole intention which is to combine a polyampholyte protected, bone marrow-derived cellular and fractional cellular material with the allograft. Moreover, this polyampholyte can be reduced by cryolyophilization, sublimation, and once reduced in volume be mixed irrespective of temperature for use as a material for bone regeneration if carrier is allograft bone, for disc regeneration if mixed with intervertebral disc allograft, for cartilage repair if combined with cartilage allograft, and for other applications attended by variation by carrier and not by process or platform.

The independent variable in the process is use of the polyampholyte as a transient or long term cryoprotectant, or a protection of bioactive potential, or a method of retaining bioavailable regenerative cytokine potency.

The polyampholyte protectant forms a strong hydrophilic characteristic of the coating to protect the cell membrane external of the whole cells. The protectant when frozen as a cryoprotectant interrupts crack propagation externally protecting the cell membrane.

In one embodiment, the biological composition has a mixture of mechanically selected biologic material derived from bone marrow. The mixture has non-whole cellular components including vesicular components and active and inactive components of biological activity, cell fragments, cellular excretions, cellular derivatives, and extracellular components. The mixture including non-whole cell fractions including one or more of exosomes, transcriptosomes, proteasomes, membrane rafts, lipid rafts might what in sum is a secretome vestment of biological potential. The mixture is compatible with biologic function.

The mixture of mechanically selected material derived from bone marrow. The biological composition preferably has bone particles. The bone particles can be added to the mixture derived from bone marrow. The bone particles include a mixture of cortical bone particles and cancellous bone particles.

The combination of non-whole cell components with a select number of non-whole cell fractions sustains pluripotency in the cells. In a preferred embodiment, the biological composition is predisposed to demonstrate or support elaboration of active volume or spatial geometry consistent in morphology with that of endogenous bone. The biological composition extends regenerative resonance that complements or mimics tissue complexity. The mixture is treated in a protectant or cryoprotectant prior to preservation or cryopreservation or freeze drying. The composition can be maintained at ambient temperature prior to freeze drying. The protectant or cryoprotectant creates a physical or electrical or chemical gradient or combination thereof for tissue regeneration. The gradient can have a physical characteristic of modulus or topography, such as charge density, field shape or cryo or chemo taxic tendencies. The gradient can have a chemical characteristic of spatially changing compositions of density or species of functional molecules, wherein the molecules can offer a fixed catalytic function as a co-factor. Also, the gradient can have an electrical characteristic of charge based or pH-based or electron affinities that confer metastability in biologic potential.

The bone marrow mixture which is derived from a cadaver has separation-enhanced non-whole cell fractions imbuing vitality including one or more of the following: separating the fractions from cells heightens their vitality, reversing "arrest" of donors, responsive molecular coupling, matrix quest in neutralizing inflammation or satience by balancing stimulus for repair. The protectant or cryoprotectant is a polyampholyte, and the nature of the required time for freezing is sufficient in having been achieved. The regenerative resonance occurs in the presence or absence of a refractory response. When using a cryoprotectant, the cryopreservation occurs at a temperature that is sub-freezing wherein the cryopreservation temperature is from 0 degrees C. to −200 degrees C. The protection may also be achieved by non-cryogenic means.

In this extension of the protection of biologic activity during preparation of an allograft, the inventors demonstrated that the cryoprotectant can be used during freeze drying to further endow the vitality of the biologic product, and that once processed as such, the requirement of sub-zero maintenance is no longer incumbent to retention of biologic function, which allows the freeze dried biologic product to be stored under ambient conditions.

Within the context of freeze drying, or cryolyophilization, it is understood that the process of dehydration effectively enhances the concentration of the liquid protectant such as polyampholyte or any other suitable protectant. This ascending concentration is a key asset to the concentration of cytokines, cell fragments, membrane components and in the choice of appropriate protectants, the translation of cryodependency as an absolute essential for preservation is shifted to an ambient environment that accesses other assets to the bioactive potential.

The biological composition's non-whole cellular component also can include organelle fragments and the active and inactive components of biological activity which can also include extant components of the human metabolome.

A method of making a biological composition of the present invention has the steps of: collecting, recovering and processing bone marrow from a cadaver donor; mechanically separating the cellular or non-cellular components or a combination thereof of bone marrow from cadaverous bone; concentrating by centrifugation and filtering; separation by density gradient centrifugation; collecting non-cellular fractions or non-cellular components or a combination thereof of predetermined density; washing the non-whole cellular fractions or non-cellular components or a combination thereof to create the mixture; quantifying concentrations of non-cellular fractions components at a non-zero entity; suspending to a predetermined concentration in a liquid protectant such as a polyampholyte cryoprotectant; freezing the mixture at a predetermined controlled rate; and packaging a bone blend having particles in the size range of 100 to 300 µm of demineralized cortical bone, mineralized cortical bone and mineralized cancellous bone either within the mixture or separate. These particle size ranges can vary higher or lower depending on the application.

Once having been frozen, the material can be stored thawed in a conventional refrigerator and at the time of use, the mixture is immersed in a warm water bath for 2-3 minutes at 37 degrees C. In this formulation, the allograft mixture with the bone marrow component that had been frozen at least once, can be diluted in saline without spinning; and then the diluted mixture, with or without the bone blend being intermixed, can be implanted by packing, injection, scaffolding or any other suitable means into a patient.

Definitions

As used herein and in the claims:

DNase—deoxyribonuclease is any enzyme that catalyzes the hydrolytic cleavage of phosphodiester linkages in the DNA backbone, thus degrading DNA.

DMEM, DMEM/LG—Dulbecco's Modified Eagle Medium, low glucose. Sterile, with: Low Glucose (1 g/L), Sodium Pyruvate; without: L-glutamine, HEPES (4-(2-hydroxyethyl)-1-piperazineethanesulfonic acid)

Dimethyl sulfoxide (DMSO) is an organosulfur compound with the formula (CH3)2SO. This colorless liquid is an important polar aprotic solvent that dissolves both polar and nonpolar compounds and is miscible in a wide range of organic solvents as well as water. It has a relatively high melting point.

DPBS—Dulbecco's Phosphate Buffered Saline.

CBT-MIXER—Mixing blade for Cancellous Bone Tumbler Jar.

Chimera—A genetic chimerism or chimera (also spelled chimaera) is a single organism composed of cells with distinct genotypes.

Cold Media—Media used during the preparation of vertebral bodies for initial processing.

"Cryomill"—The CryoMill is tailored for cryogenic grinding. The grinding jar is continually cooled with liquid nitrogen from the integrated cooling system before and during the grinding process. Thus the sample is embrittled and the chemical composition is preserved. The liquid nitrogen circulates through the system and is continually replenished from an Autofill system in the exact amount which is required to keep the temperature at −196° C. Powerful impact ball milling results in a perfect grinding efficiency. The Autofill system avoids direct contact with LN2 and makes the operation very safe. Its versatility (cryogenic, wet and dry grinding at room temperature) makes the CryoMill the ideal grinder for quantities up to 20 ml. The grinding jar of the CryoMill performs radial oscillations in a horizontal position. The inertia of the grinding balls causes them to impact with high energy on the sample material at the rounded ends of the grinding jar and pulverize it. The grinding jar is continually cooled with liquid nitrogen from the integrated cooling system before and during the grinding process.

Cryopreserved-Tissue frozen with the addition of, or in a solution containing, a cryoprotectant agent such as glycerol, or dimethylsulfoxide, or carboxylated poly-1-lysine, or trehalose, or other molecular hydrogel preservatives that might be derived from core chemistry analogues or families of biochemical similarity.

"Disc Desiccation"—Disc desiccation is an extremely common degenerative change of intervertebral discs.

The incidence climbs with age, and to a large degree a gradual desiccation is a 'normal' part of disc aging. It results from replacement of the hydrophilic glycosaminoglycans within the nucleus pulposus with fibrocartilage, and the reduction of charged moieties that bind and structure water, and the subsequent loss of water from the disc.

"Freeze Drying"—Freeze-drying, also known as lyophilization, lyophilization, or cryodesiccation, is a dehydration process typically used to preserve a perishable material or make the material more convenient for transport and stable at room temperatures in an appropriate contained or package. Freeze-drying works by freezing the material and then reducing the surrounding pressure to allow the frozen water in the material to sublimate directly from the solid phase to the gas phase.

Freeze Dried/Lyophilized—Tissue dehydrated for storage by conversion of the water content of frozen tissue to a gaseous state under vacuum that extracts moisture.

"Hypothermic Dehydration"—hypothermic dehydration depends on placing the object at reduced temperatures above freezing point into a high vacuum chamber allowing it to dry to a desired residual moisture level. The result is dried tissue without fissures, microscopic ice crystal distortion and collapse phenomenon.

Normal Saline—0.9% Sodium Chloride Solution.

"Nucleus Pulposus"—Nucleus pulposus is the gel-like substance in the middle of the spinal disc. It is the remnant of the notochord. It functions to distribute hydraulic pressure in all directions within each disc under compressive loads. The nucleus pulposus consists of large vacuolated notochord cells, small chondrocyte-like cells, collagen fibrils, and proteoglycan aggrecans that aggregate through hyaluronic chains. Attached to each aggrecan molecule are the glycosaminoglycan (GAG) chains of chondroitin sulfate and keratan sulfate. Aggrecan is negatively charged, allowing the nucleus pulposus to attract water molecules. The amount of water and glycosaminoglycans decreases with age and degeneration.

Packing Media—Media used during initial processing and storage of the processed vertebral bodies prior to bone decellularization.

PBS—Phosphate Buffered Saline.

Processing Media—Media used during bone decellularization that may contain DMEM/Low Glucose no phenol red, Human Serum Albumin, Heparin, Gentamicin and DNAse.

"Proteoglycans"—Proteoglycans are proteins that are heavily glycosylated. The basic proteoglycan unit consists of a "core protein" with one or more covalently attached glycosaminoglycan (GAG) chain(s). The point of attachment is a Serine (Ser) residue to which the glycosaminoglycan is joined through a tetrasaccharide bridge (e.g. chondroitin sulfate-GlcA-Gal-Gal-Xyl-PROTEIN). The Serine residue is generally in the sequence -Ser-Gly-X-Gly- (where X can be any amino acid residue, but Proline), although not every protein with this sequence has an attached glycosaminoglycan. The chains are long, linear carbohydrate polymers that are negatively charged under physiological conditions, due to the occurrence of sulfate and uronic acid groups. Proteoglycans occur in the connective tissue. Proteoglycans are a major component of the animal extracellular matrix, the "filler" substance existing between cells in an organism. Here they form large complexes, both to other proteoglycans, to hyaluronan and to fibrous matrix proteins (such as collagen). They are also involved in binding cations (such as sodium, potassium and calcium) and water, and also regulating the movement of molecules through the matrix. Evidence also shows they can affect the activity and stability of proteins and signaling molecules within the matrix. Individual functions of proteoglycans can be attributed to either the protein core or the attached GAG chain and serve as lubricants.

BRIEF DESCRIPTION OF THE DRAWINGS

The patent or application file contains at least one drawing/photograph executed in color. Copies of this patent or patent application publication with color drawing(s) will be provided by the Office upon request and payment of the necessary fee.

The invention will be described by way of example and with reference to the accompanying drawings in which.

DETAILED DESCRIPTION OF THE INVENTION

Figure 1:
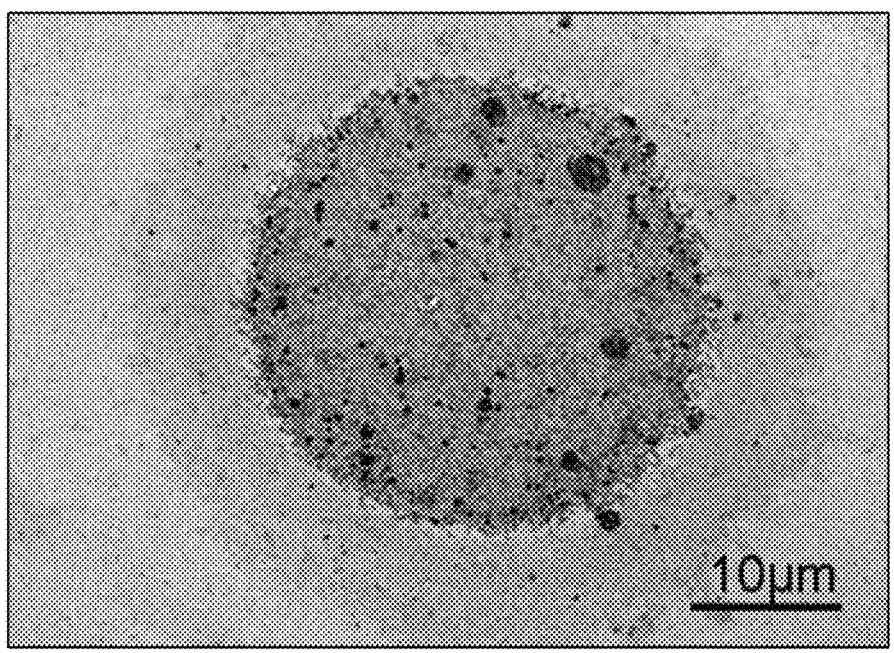
FIG. 1. Is an image derived from work done in 1975 that demonstrates the electro-dense halo of poly-lysine represented by transmission electron microscopy (TEM) following use of a coating on plates to facilitate attachment.

Vivex, the assignee of the present invention with its scientific research team of inventors has established itself as a preeminent manufacturer of advanced allograft biologic materials to support regenerative medicine initiatives. Vivex licensed a bone marrow cell line that was characterized with marrow-isolated adult multi-lineage inducible characteristics from the University of Miami. This patent publication, US 2015/0132266 A1, allowed for manufacturing and expansion, and has since been advanced to include a broader scope based on non-whole cell fragments including extracellular vesicles, as disclosed in U.S. Pat. Nos. 9,675,643 B2 and 9,687,511 B2, the contents of which are being incorporated by reference in their entirety herein.

Vivex additionally licensed U.S. Pat. No. 9,603,355 B2 for an amino acid polymer primarily defined as a polylysine. While other amino acids are included as substitutions in the composition, other properties of the materials defined in this patent have been observed. In addition to protecting the cells from freeze damage during storage, the formulation has been shown to be an effective tool for harvesting exosomes and enshrouding them as well. More recent work has shown that whole cells shrouded in the cryoprotectant exhibit unique and quite unexpected characteristics during preservation and later implantation.

The inventors developed several different processes for cell protection with this cryoprotectant, which have included a non-whole cell, and a bio-energized combination that used various fields of mechanical, electrical, and photonic stimulation to enhance the cell differentiation and activate the cells. One of the principal differences in those two products has been attributable to pH variation, and resulted in vastly different viable cell determinations on thawing. The lower pH in the first version of the cryoprotectant was 4.5-5.4 and generally formulated as less compatible with cell survival. What was impressive however, was the fact that the clinical performance has been outstanding and approaching 97% in the first 16,000 uses of the VIA® Graft product in patient care. The current composition of the present invention is developed to have a pH of 7.4 which is metabolically and physiologically more appropriate for cell survival, and functionally attunes the polyampholyte to appropriately balanced and structured cationic and anionic moieties.

Although previous prior art patents have assumed that the material protection primary purpose of cryoprotectants, such as DMSO based, has been to reduce, or eliminate crack propagation from ice crystal damage during freezing, the requirement for washing and decanting prior to use resulted in these protectants being washed away prior to implantation or culturing of the cells. The inventors of this invention have believed the explanation for clinical performance was stemming from coating the material with a protectant suitable for direct implantation. Other observations, recently made, have supported the hypothesis that the coating affects cell shape and that when coated, the cells do not flatten and attach when put in culture; instead they remain round. At first glance, the lack of attachment lead to the presumption that the cells are not viable, but confirmation with cell markers indicated they are alive, remain potent, and simply are not guided to attachment, this was a totally unexpected finding.

Cell attachment, long been accepted as a metric of affinity, depends on charge variation, surface roughness, material composition, and several studies have shown that modification of surfaces can be used to optimize biological activity. Limiting the discussion to the cryoprotectant, the scientific community has understood for some time that charge can be used to influence attachment and guided by surface affinity between the cell membrane and surface features, it is possible to tune the interaction between cells and surfaces to the extent that differentiation and proliferation can be tailored to specific lineage in cell phenotype, and in aggregate to attend tissue and organ morphology.

In the course of developing the use of the cryoprotectant of the present invention, solving initial challenges lead to better understanding novel properties that had not been defined in patents concerning cryoprotectants. The earlier work adjusted transition and thawing but did not identify assets to buffer inflammation, reduce premature differentiation, sustain regenerative potential, and facilitate donor-host interface during implantation of the grafting materials as was discovered in the present invention.

That course of initial development also provided an indication that the collection of the material from a low viability thaw contained a high level of exosome material that when added to a separate culture provided a stimulus to those cells from the exposure to the non-whole cell contents of the first low viability thawed material.

The key asset of coating the cells is derived from the cell attachment to the cryoprotectant. Using a polyampholyte to neutralize the hydrophilic amide linkage, a strong hydrophilic bond is established that protects the cell membrane, and provides a stable interface with environments external to the cells. This cell membrane boundary conditioned by the protectant at this material interface with the aqueous external milieu has been shown to interrupt crack propagation and in that way externally protects the continuity of the cell membrane. Additional value was sought to overcome the DMSO cryoprotectant issues of toxicity that lowers cell viability, and calls for a decant and rinse step before clinical use. These two properties guided the inventors' choice to adopt the technology and commercialize as a best in class Cellular Bone Allograft for bone regeneration applications.

Achieving that understanding also allowed us to recognize value in room temperature exposure of the polyampholyte treated biologic materials and that the loss of cell viability in process can accent the collection of biologically active sub-cellular fractions simultaneously.

During the testing and developing of quality guidelines, the lack of cell attachment in culture, the unusual round cell morphology, and the challenges of assaying viability presented new challenges to the inventors. However, in the process of defining those parameters and establishing quality assurance and product release standards, the inventors gained new insight into the cryoprotectant that the charge of a carboxylated poly-lysine polyampholyte protectant provides the cells an attachment paradigm that without apical-basal polarization retards flattening and keeps the cells round. With molecular surfaces, or simulated attachment facilitated by binding ligands surrounding the cell, a second advantage to the cells emerges that supports the fact that during early inflammation phases of the wound repair, donor, or implanted cells are not exposed to granulation tissue cytokines. Without this early exposure, and in absence of attachment, cytokines that nurture regeneration rather than fibroblast proliferation are the more effective modulator of the live cell fraction. A two-dimensional image derived from work done in 1975 demonstrates the electro-dense halo of poly-lysine represented by transmission electron microscopy (TEM) following use of a coating on plates to facilitate attachment (FIG. 1). The relevance of this image in comparison to a recent Scanning Electron Microscope (SEM) is remarkable.

In the case of material collected using the polyampholyte to protect the subcellular, and non-whole cell fractions, the high affinity for cells offered by the protectant extends benefit to the host cells during allograft placement. Mixtures of the protectant with the allograft and contents of the biologically active contents serve an important function of transferring preferential potential to host cell regenerative inertia.

Figure 2:
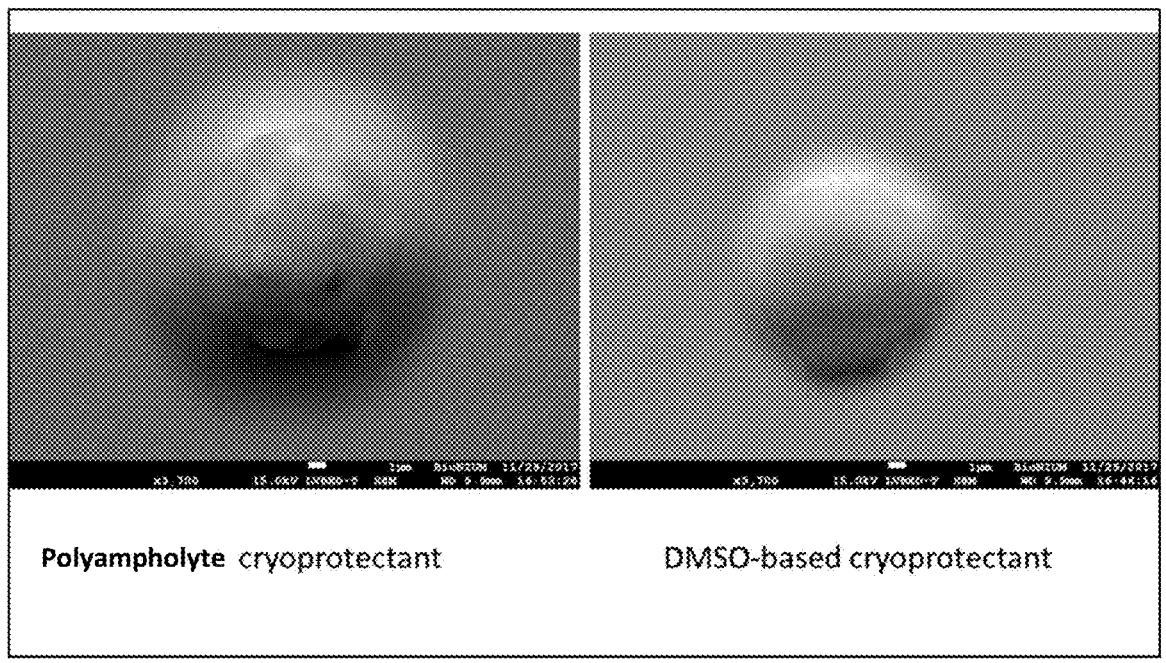
FIG. 2 is a comparison of a polyampholyte protected cell on the left and a DMSO treated cell on the right.

What makes the observation impressive emerges in the context of the recent scanning electron micrograph where the 3D structure that is presented, starkly contrasts the difference between the polyampholyte cryoprotectant treated cells and DMSO treated cell lines. The abundance of charged field is appropriate to a polyampholyte which provides a charge (FIG. 2). These cationic coatings, including poly-lysines were developed for positive charge—essentially to facilitate the electronegative charge on cells to be more avidly bound.

Figure 3:
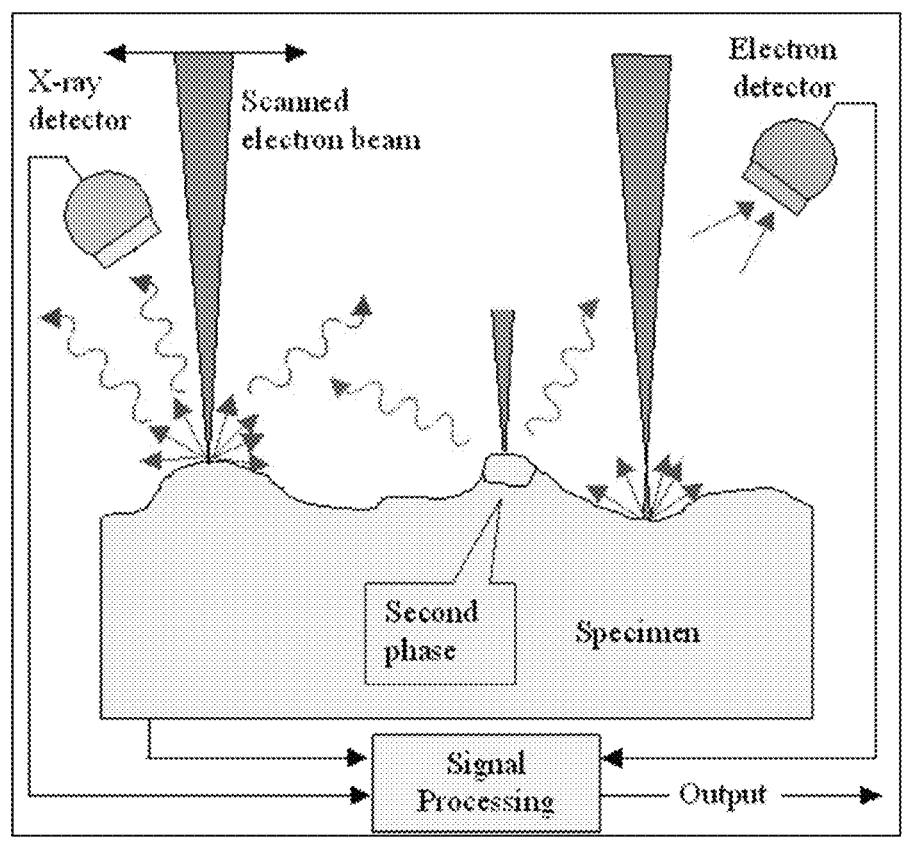
FIG. 3 is a schematic depiction of how a SEM, scanning electron microscope 3D image is produced.

Scanning electron microscopy is an accepted tool for evaluating structure, composition, and even isotope variations of materials. While the theoretical design straightforward, shown schematically in FIG. 3, there are many intricacies to the analysis that can be accounted.

The evaluation of the viable cell product compositions developed by the inventors, provided additional insights that refine expectations for protection, and extend additional benefits.

Various protective roles of the cryoprotectant include protection from freeze-thaw damage; crack propagation inhibition; insulation from early inflammation following transplantation; retention of non-differentiated cell phenotype; attachment protection—delayed flattening of cells following implantation; donor—host contact facilitation; paracrine exchange; metabolic neutrality; and cationic pharmacology enhances cell attachment.

Several observations have been developed by the present inventors to account for these additional benefits: The cryoprotectant completely envelops the cells. Polyampholyte materials retain intense, but balanced charge when used to protect the cells. This charge is evident in SEM images. Cells retain viability and sense attachment even though still round. The protectant of the present invention protects the cells whereas DMSO is not retained on the cells for protection. The protectant remains surrounding the cells for up to 6 days, is normally metabolized, and protects transplanted cells from macrophage digestion during the granulation phase of inflammation and wound healing in contrast to the DMSO protected cells that are rinsed removing the protectant and thus exposing the cells to this condition at the onset of implantation.

This benefit is conferred irrespective of the whole cell fraction. Although the presumption has been that cellular bone matrices functionally improve regenerative potential by attaching, integrating, and functioning in concert with host tissue and cells, several leaders in the regenerative medicine field have publicly stated and published opinions that less than 4% of the cells survive and engraft. In many respects this seems a wholesale structuring of a negative argument with 95% probability that no cells survive, but as tracking in clinical care, and biopsy are improbable tools for assurance this stands as a basic definition that proponents of regenerative therapeutic utilization count more on the paracrine activity of the donor than the cell itself to be responsible.

To better clarify the discovery process and further a basis for claims of the present invention, it is important to understand the methods and directions that have guided new understanding and directed additional invention.

Figure 4:
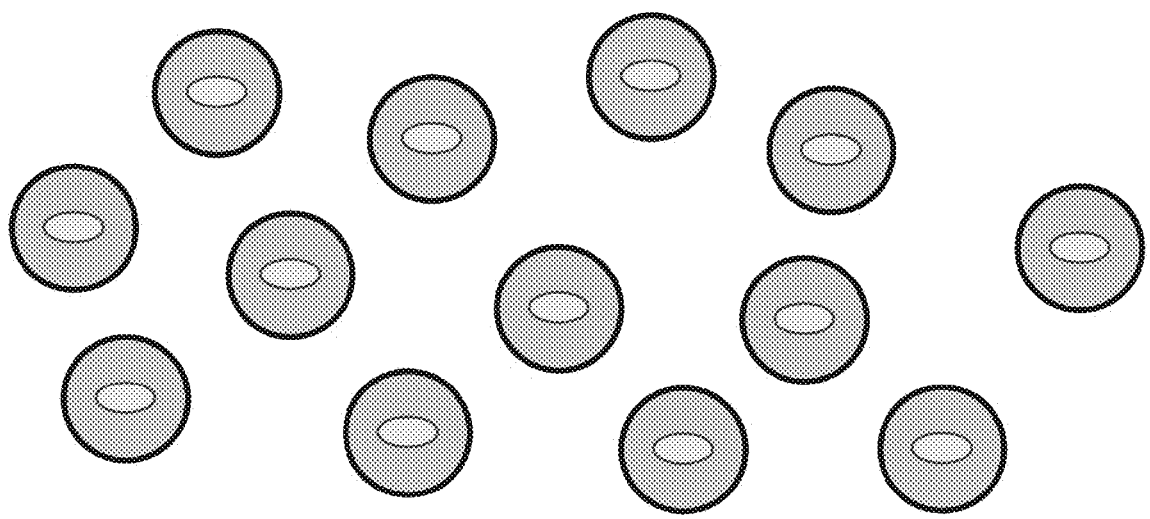
FIG. 4 is a depiction of cells isolated during the process.
Figure 5:
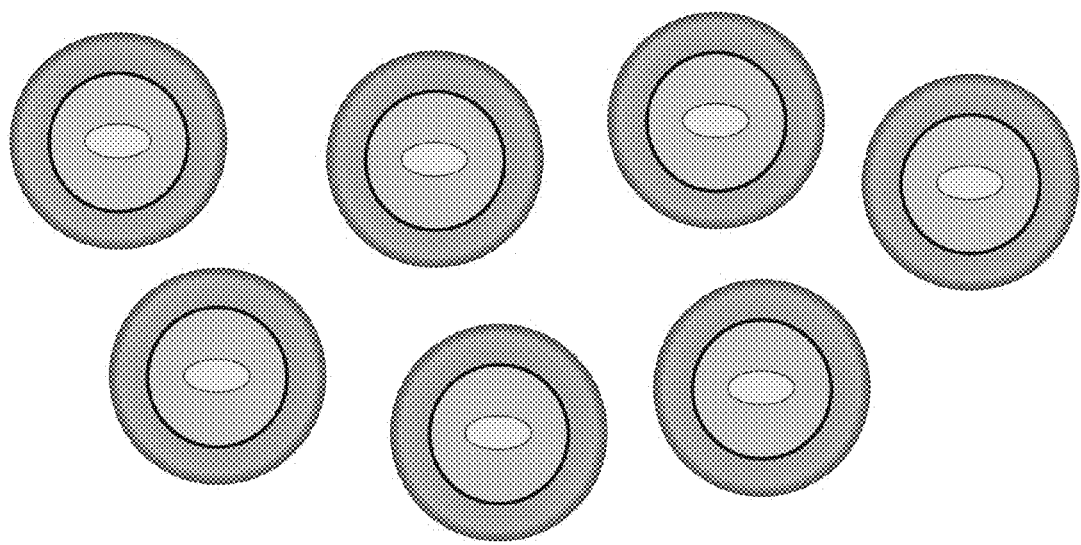
FIG. 5 is a depiction of cells coated in cryoprotectant.
Figure 6:
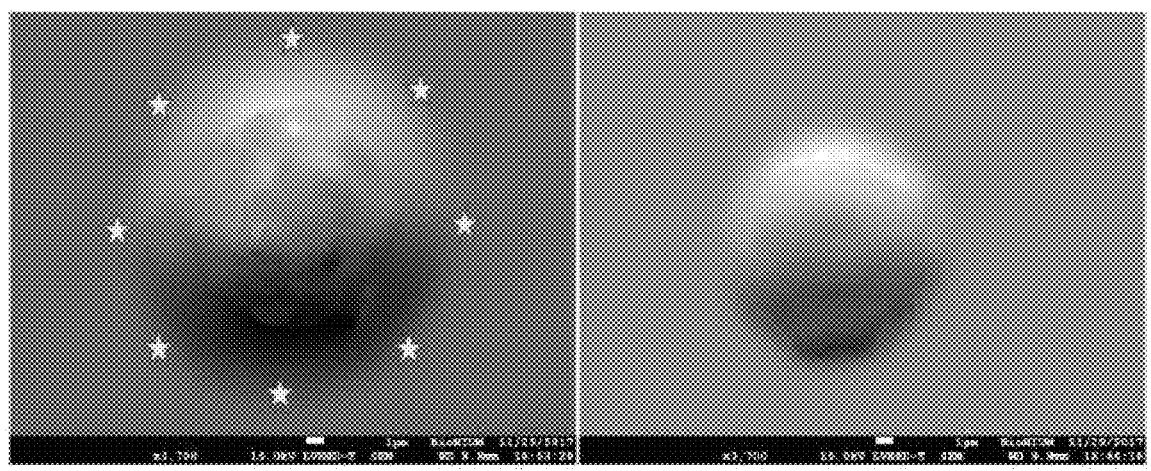
FIG. 6 is a SEM image showing the electron dense halo (shroud) on the polyampholyte protected cell on the right and a DMSO treated cell on the right.
Figure 6:
Figure 7:
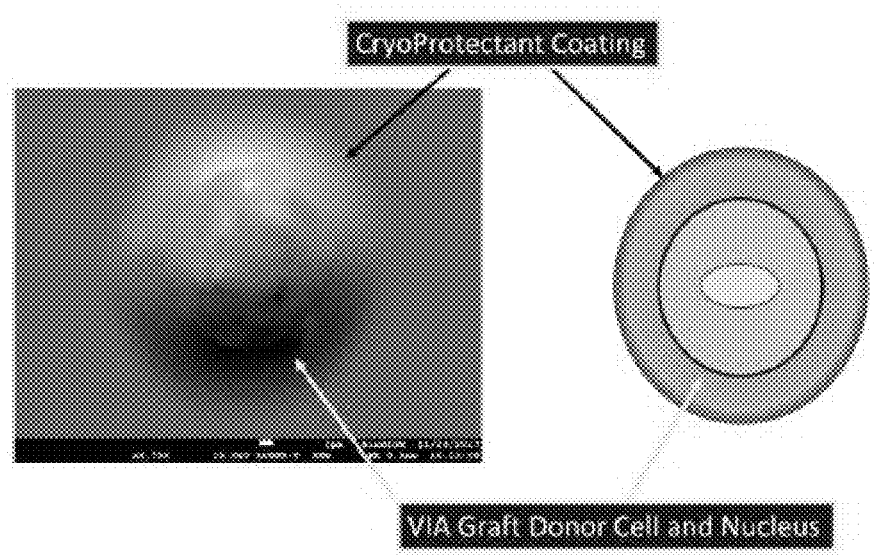
FIG. 7 shows a depiction of the halo.

In one exemplary embodiment, the first steps in developing the cellular bone matrix is to separate bone marrow cells. This is well defined and has been extended to include not only whole cells, but also cell fragments, vesicles, ligands, lipid rafts, exosomes, organelles etc. Each permutation has been paired with a broad term for the cryoprotectant, polyampholyte. FIGS. 4 and 5 illustrate the cells isolated during the process and the cells coated in the cryoprotectant. Note the halo surrounding the cells. In addition to providing protection from crack propagation as intended from its use in cell preservation, this electro positive surrounding field of charge also offers several benefits to the cell during placement, to the host during chemotaxis, and to the regenerative construct during cell-cell communication and paracrine intercellular exchange.

The first observation of the development was that the cells did not plate, and while viability was apparent, the floating, equibuoyancy of the cells in the medium did not match any available cell culture literature. The cells were alive as determined by fluorescent nuclear markers, but did not allow trypan blue or other cellular viability markers to be used with any assurance. However, after several days in culture and with support of cell media, cells did begin to flatten, attach and assume the morphology of cells better typified as mesenchymal stem cells (MSC). These cells also could be identified using flow cytometry to bear common ligands that are consistently shown to be a part of MSC known markers.

The gulf guiding the proof is part of the new understanding that in part forms the basis for this invention. A highly charged coating used to protect the cells also creates a cell surface, cell matrix bond that makes the cells think they are attached. Rather than flattening to one surface, the cells remain completely surrounded by a high affinity binding that protects from freezing, but more importantly buffers the cells from the surrounding materials during placement or implantation.

Figure 8:
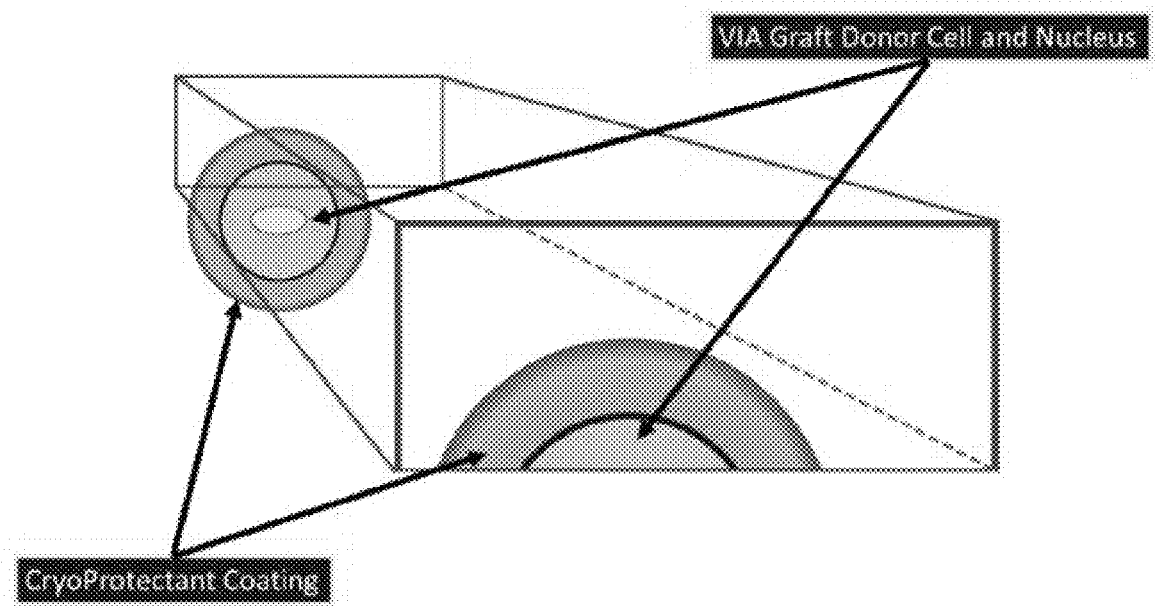
FIG. 8 is a depiction of the cryoprotectant coated cells.

There are actually two phases of inflammation that take place during wound healing, and despite the careful controlled situations of surgery the intervention is still a wound that requires repair and integration. The first phase is the initiation phase that causes the heat, pain, swelling, and redness associated with inflammation. Subsequently, there is a second phase called the resolution phase that reverses the initiation phase and allows tissue regeneration. As long as these two phases of inflammation are balanced, healing occurs. One of the clear and distinct advantages of the coating of cryoprotectant is its ability to surround and protect during the early phase of inflammation. Rather than driving the viable cell phenotype of the donor in response to the catabolic cytokines, the shielding instead allows the cells to be exposed to the subsequent regenerative formation, shown in FIG. 8.

Figure 9:
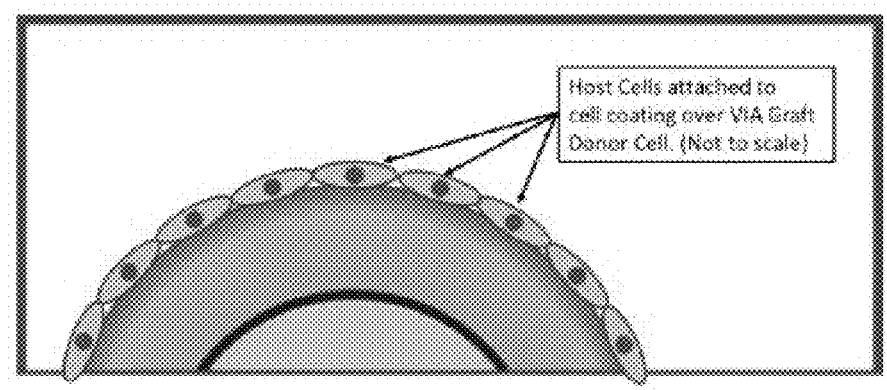
FIG. 9 is a schematic flow chart showing the host donor cell relationship with host cells attached to the cell coating shroud, the donor cells and host cells, as illustrated, are not to scale.
Figure 10:
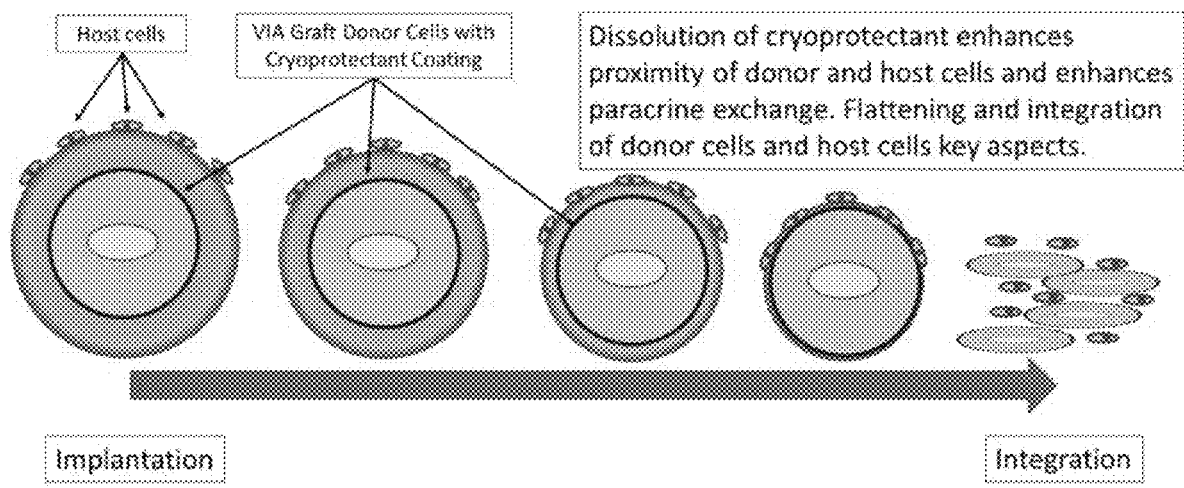
FIG. 10 shows the metabolic absorption of cryoprotectant.

Secondary to the protection afforded the donor cells, the host tissue also is able to attach to the coating and this brings the donor and the host cells in close proximity during the regenerative phase. This close proximity is effective in facilitating the paracrine interface that further stimulates and integrates the regenerative response as shown in FIGS. 9 and 10. The host cells are intentionally shown smaller in size compared to the donor to illustrate the attaching to a donor cell, in reality, the host cells are typically the same size of the donor cell as evidenced in FIG. 11.

This feature is independent of the viability, dependent on the polyampholyte, but wholescale integrated into the process and protection afforded by the polyampholyte and the process of freezing during the manufacturing.

Figure 11:
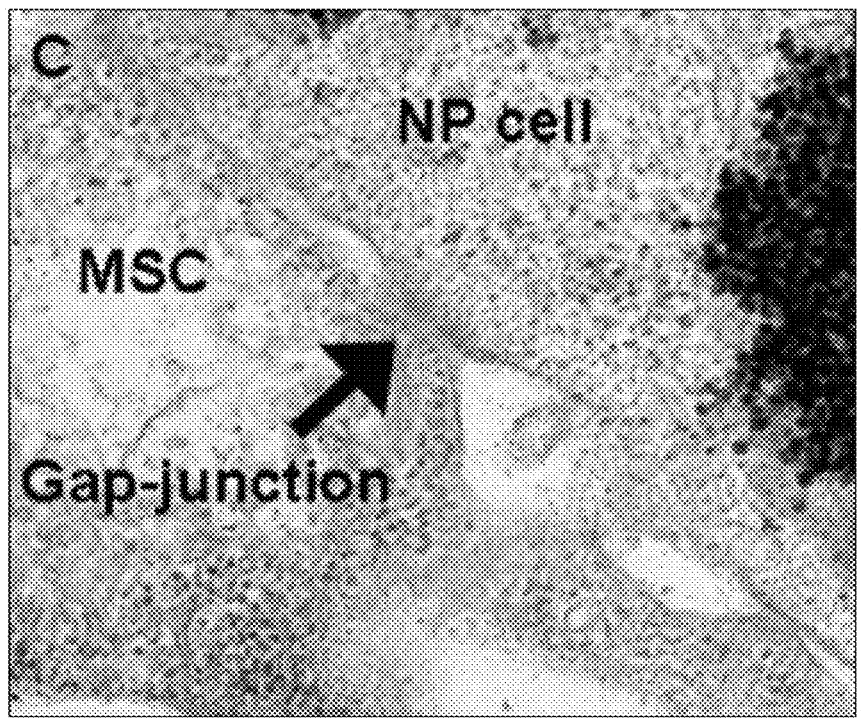
FIG. 11 shows the cell exchange of exosome from "Bi-Directional Exchange of Membrane Components Occurs during Co-Culture of Mesenchymal Stem Cells and Nucleus Pulposus Cells" by Sandra Strassburg, Nigel W. Hodson, Patrick I. Hill, Stephen M. Richardson, Judith A. Hoyland.

Metabolism of the coating results in approximation of host cells attached with donor cells that are coated. As the cells come together, current understanding supports the fact that genetic material is exchanged. By providing a cryoprotectant surrounding the donor cells, and also defining a composition that accentuates attachment of host cells, a novel new use is identified that refines and optimizes direct cell connections for epigenetic exchange. This is shown in FIG. 11.

Figure 12:
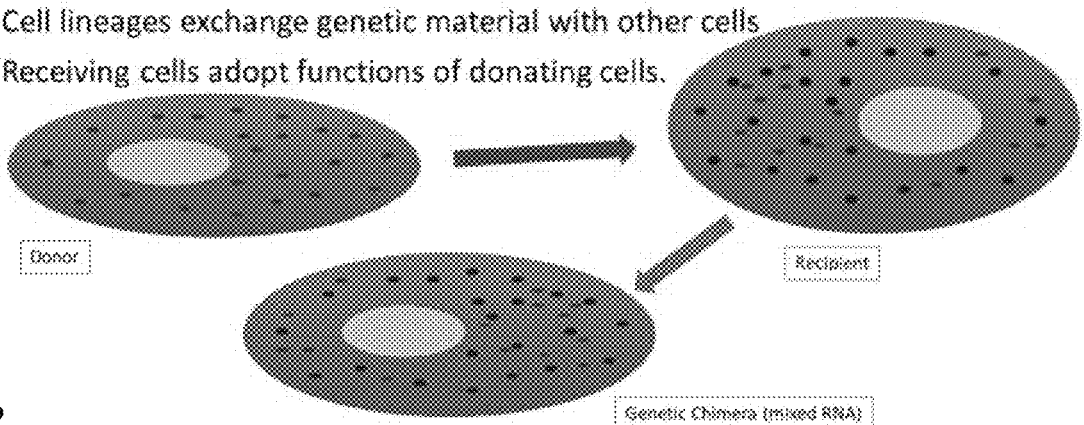
FIG. 12 shows the principle of genetic transfer with colored representing the difference and gain of function.

The theory behind exosome expansion and epigenetic regulation has evolved to the point that molecular tracking occurs and can be shown between cells. Depicted in FIG. 12, the colored dots represent difference and the gain of function the bi-colored inclusions. The donor cell exchanges material such as exosomes with a host or patient's cell. On cell division, a genetic chimera (mixed RNA) cell has the genetic encoded material of both cells. This is extremely beneficial to cell replication during the healing process.

Figure 13:
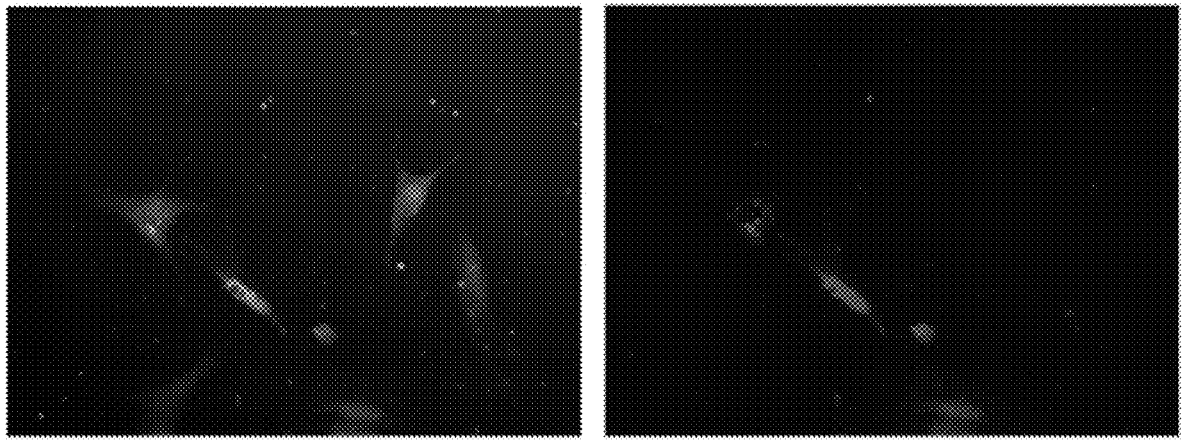
FIG. 13 shows how co-culture exchange is demonstrated with CFDA staining on the left in green and Dil staining on the right in red.
Figure 14:
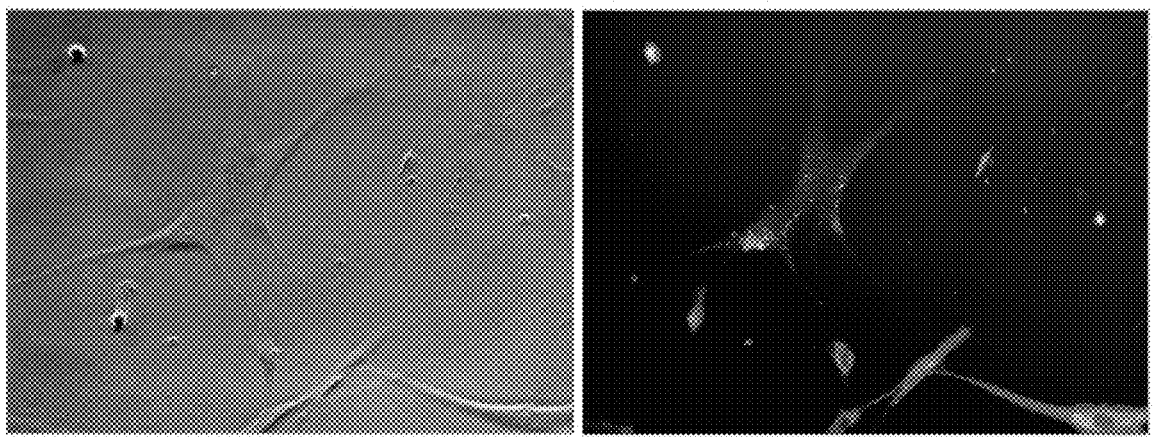
FIG. 14 shows evidence of genetic exchange of intracellular material after 3 days of co-culture.

FIG. 13 provides laboratory evidence of co-culture exchange with mesenchymal cell population expanded and divided into two equal portions. One portion stained with for exosome membrane DIL and Second portion stained with cytoplasmic stained CFDA (Carboxyflourescein diacetate). While FIG. 14 shows 3 days of co-culture evidence of genetic exchange demonstrated exchange of intracellular material, these figures together confirm the findings and are significant to the current understanding of the present invention.

For completeness of the understanding of the invention as described above, an example of one method of recovering the biological material from bone marrow is disclosed. It is understood that other sources and methods can be used to collect biologic material such as from bone, blood, fat cells, including the isolating of whole cells from these alternative sources from living hosts or cadavers and these cells would equally benefit from the present invention.

With reference to the exemplary method which is a tissue regenerative biological composition made from bone marrow 200, it is believed best understood by the methods used to process and recover the biological composition, as illustrated in the FIGS. 15-20.

Figure 15:
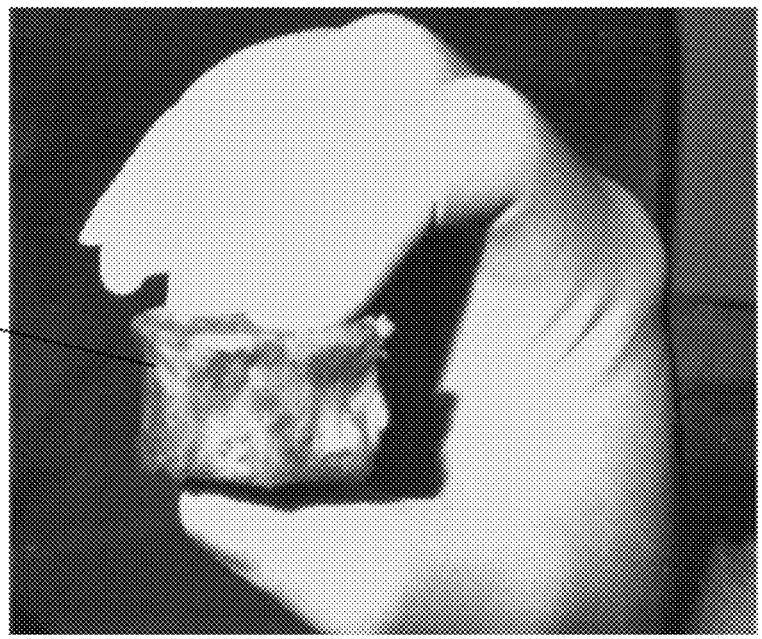
FIG. 15 shows a photograph of a cut vertebral body taken from a spine of a cadaver donor.
Figure 16:
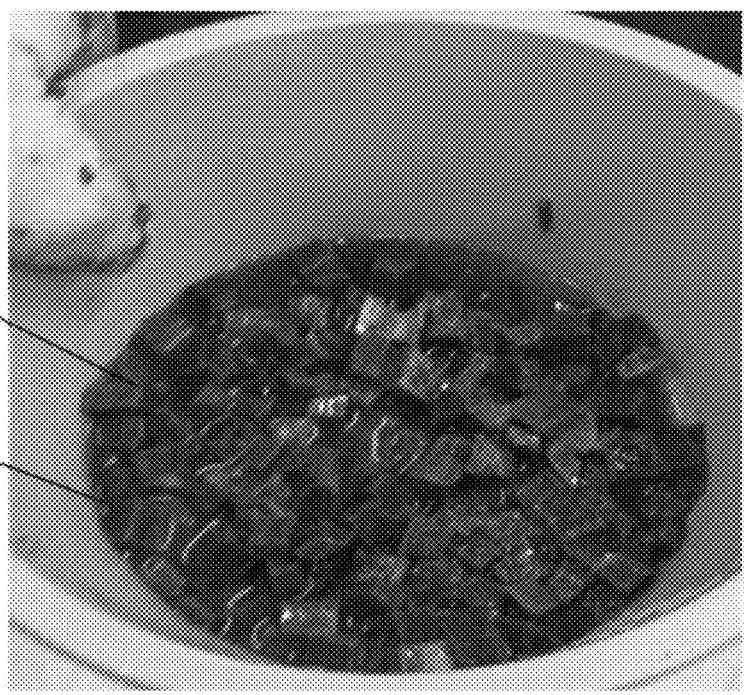
FIG. 16 shows a photograph of the vertebral body after being cut into cubic pieces and immersed in a packing media.
Figure 17:
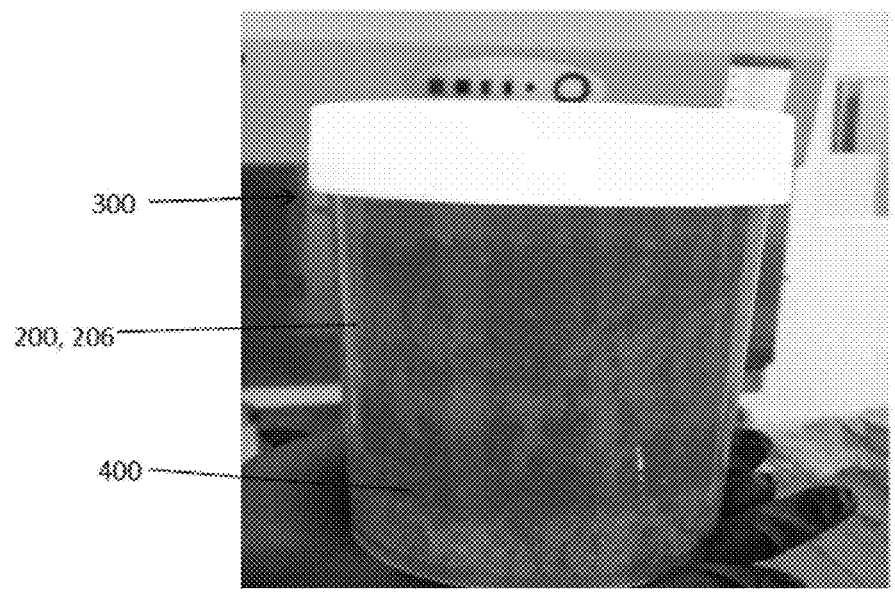
FIG. 17 shows a photograph of the bulk bone material after being ground and immersed in packing media and placed in a jar for later tumbling.
Figure 18:
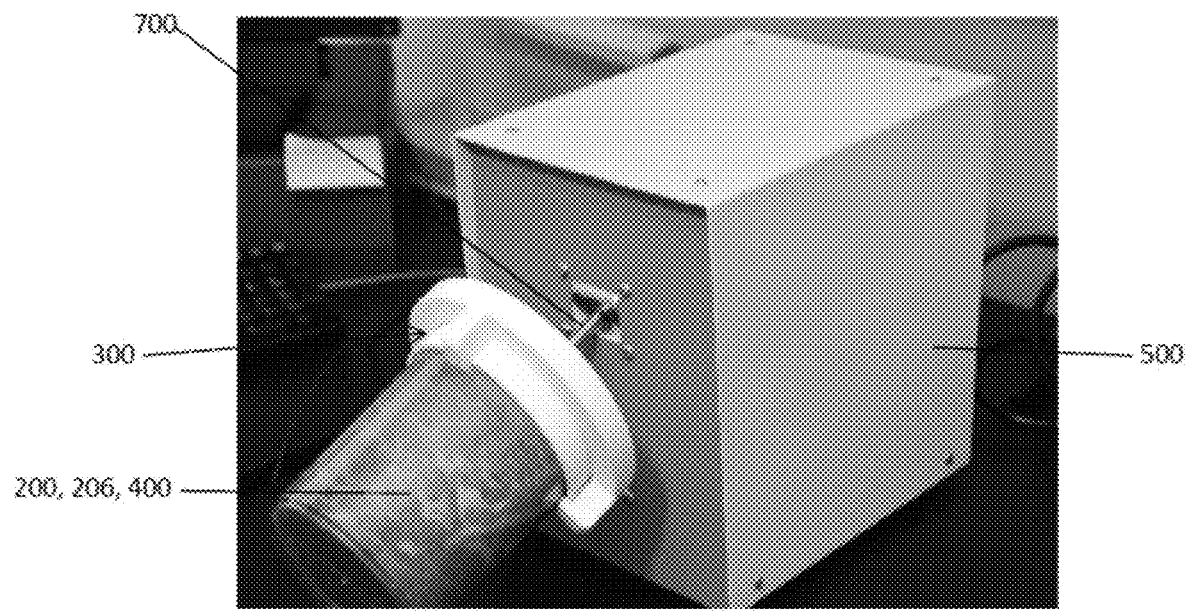
FIG. 18 shows a photograph of the jar with a CBT-Mixer connected to a tumbler.

The first steps are to collect, recover and process bone marrow 200 from a cadaver donor. To do this, the spine is removed aseptically from the cadaver and the resultant spine segment is covered by cold media. The cold media has 0.5 ml of Heparin; 10,000 units/ml per 500 ml of DMEM. DMEM is a sterile solution with low glucose (1 g/L), Sodium Pyruvate; without L-glutamine, or HEPES. This cold media is used for packaging the spine segments for later processing. At this point the spine segment includes a plurality of vertebral bodies 202. The clinical technician must remove as much soft tissue as possible and cut each vertebral body 202 with a saw. These vertebral bodies 202, once cleaned, of all adherent soft tissue around the cortical surfaces will look as shown in FIG. 15.

Once a cleaned vertebral body 202 is obtained, the next step involves cutting each vertebral body 202 into pieces, each piece 204 roughly 1 cm$^3$. The cut pieces 204 being immersed in a packing media 400. The exemplary packing media can be DMEM with 0.5 ml Heparin and 1.25 ml of DNAse added.

Once all the vertebral bodies 202 have been cut, the pieces 204 are taken to the bone grinder. The bone is ground into 4-10 mm pieces using packing media 400 to help the pieces go through the grinder. The ground bone 206 (bulk cortical-cancellous crushed) and all of the packing media 400, estimated volume of 500 ml are transferred into a jar 300 where 0.5-1.0 ml of Gentamicin is added to the jar 300 with ground bone 206 and packing media 400. At this point, the crushed bone 206, including cellular soft marrow 200, is intermixed.

Figure 19:
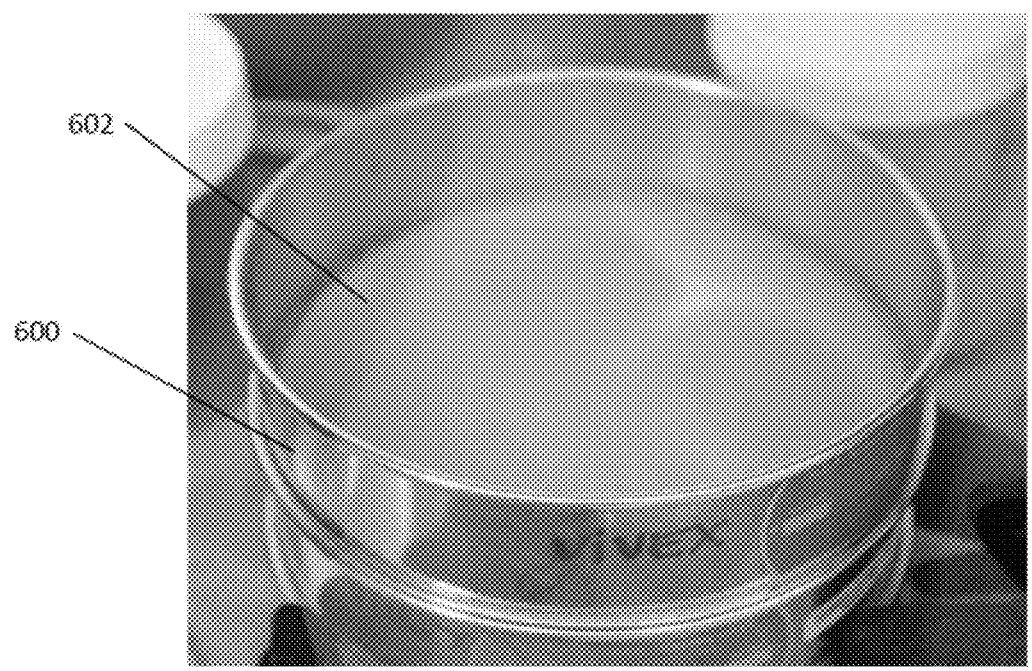
FIG. 19 is a photograph of an exemplary sieve device having sieves sized to separate the solid material.

The step of mechanically separating these cellular components of bone marrow 200 from the cadaverous bone is next performed. Transferring the bulk cortical-cancellous bone chips into a new jar with a CBT-Mixer in the jar. The bulk cortical-cancellous bone chips 206 will go through four cycles as summarized in the table below. Each cycle, after cycle 1, contains three steps using a bone tumbler 500 and sieve set 600. The sieve set 600 has screens 602 of various sizes, for example 500 μm and 180 μm, as shown in FIG. 19.

| Step | Cycle 1 | Cycle 2 | Cycle 3 | Cycle 4 |
|---|---|---|---|---|
| Bone Tumbler | 30 minutes. Using 500 mL Processing Media | 30 minutes Using 500 mL Processing Media | 30 minutes Using 500 mL Processing Media | 30 minutes Using 400 mL Processing Media |

-continued

| Step | Cycle 1 | Cycle 2 | Cycle 3 | Cycle 4 |
|---|---|---|---|---|
| Sieve Set | Use the 500-μm and the bottom pan sieve. Discard decanted fluid. | Use the 500-μm, 180-μm and bottom pan sieve. Collect decanted fluid. | Use the 500-μm, 180-μm and bottom pan sieve. Collect decanted fluid. | Use the 500-μm, 180-μm and bottom pan sieve. Collect decanted fluid. |
| Centrifuge | N/A | Use decanted fluid. | Use decanted fluid. | Use decanted fluid. |

Figure 21:
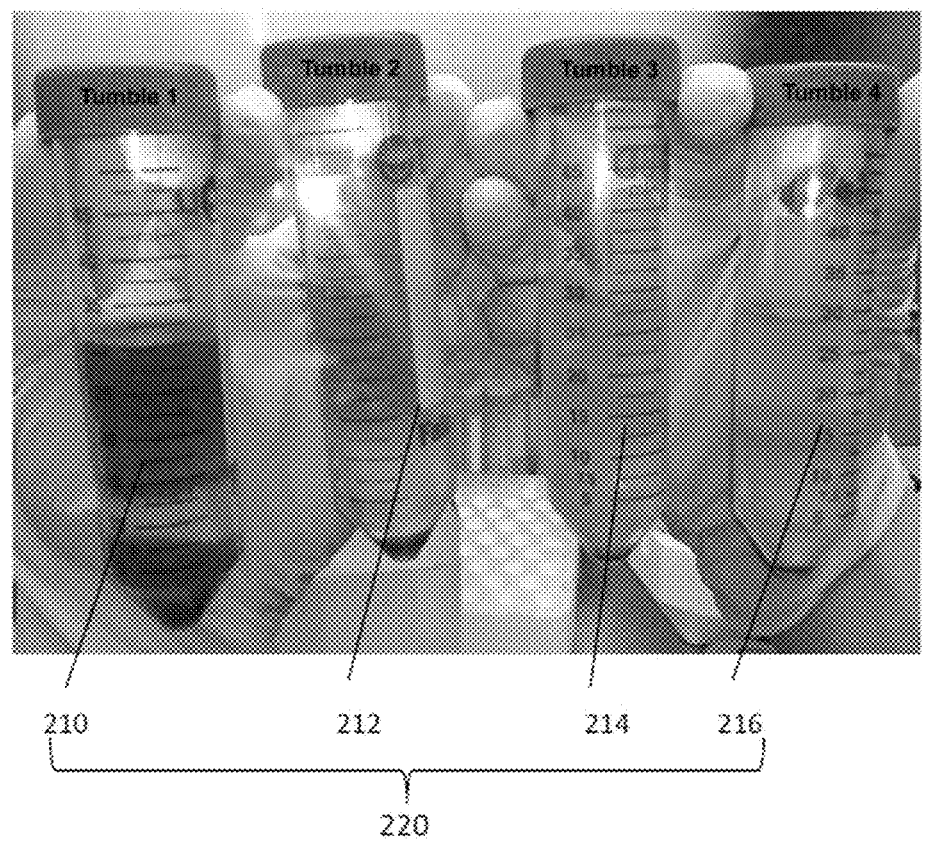
FIG. 21 is a photograph showing the four tumbling steps 1-4 by exemplary collection and Ficoll separation of the decanted fluids, the fluid in tumble 1 being completely discarded to remove unwanted debris.

In cycle 1, the decanted fluid 210 is discarded. To best understand this, an exemplary FIG. 21 shows conical tubes with the decanted fluids after each cycle followed by Ficoll separation, the Ficoll being a polysaccharide, sucrose, containing cushion that forms the density gradient. Tumble 1 or Cycle 1 has most of the unwanted cells and debris as evidenced by its dark and red appearance whereas each subsequent cycle 2, 3 and 4 are progressively cleared. This FIG. 21 is only to illustrate the effects of multiple tumbles 1-4 and the value in discarding the decanted liquid 210 after the first tumble 1.

After each subsequent sieving of the bulk bone material 206, the decanted fluid 212, 214, 216 containing the mixture with whole cells is collected and put into a collection jar. When the next three cycles are complete and the decanted fluid is all placed in the collection jar comingling the fluids 212, 214 and 216 to form a decanted fluid 220. Then the centrifugation of the combined decanted fluid 220 occurs by placing the fluid 220 in a number of 250 ml conical tubes using a 100 ml pipette. The centrifuge is programmed to 280×g for 10 minutes at room temperature, preferably about 20 degrees C. The fluid 220 is passed through a blood filter to further remove any bone or spicules or clumps from the suspended cells. This completes the step of centrifuging and filtering. At this point, the mixture including whole cells 240 has been separated from the soft marrow tissue 200 and the remaining cancellous and cortical bone is discarded.

Figure 20:
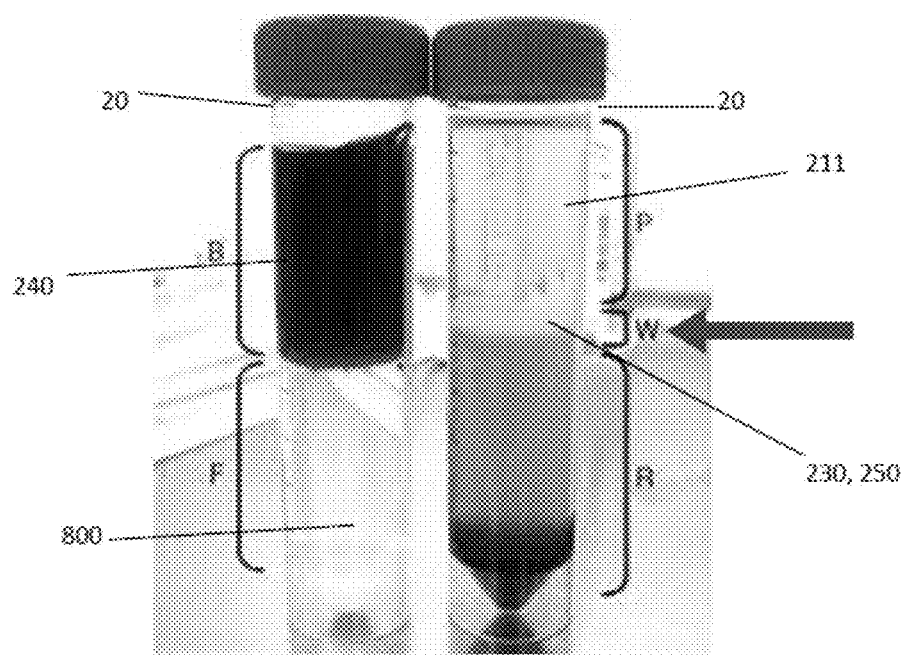
FIG. 20 shows a photograph of two 50-ml vials, the one on the left being prior to centrifuging with the Ficoll that is commercially available at the bottom and the material above it. The 50-ml vial on the right is after centrifuging showing the non-whole cell fraction interface layer.
Figure 22:
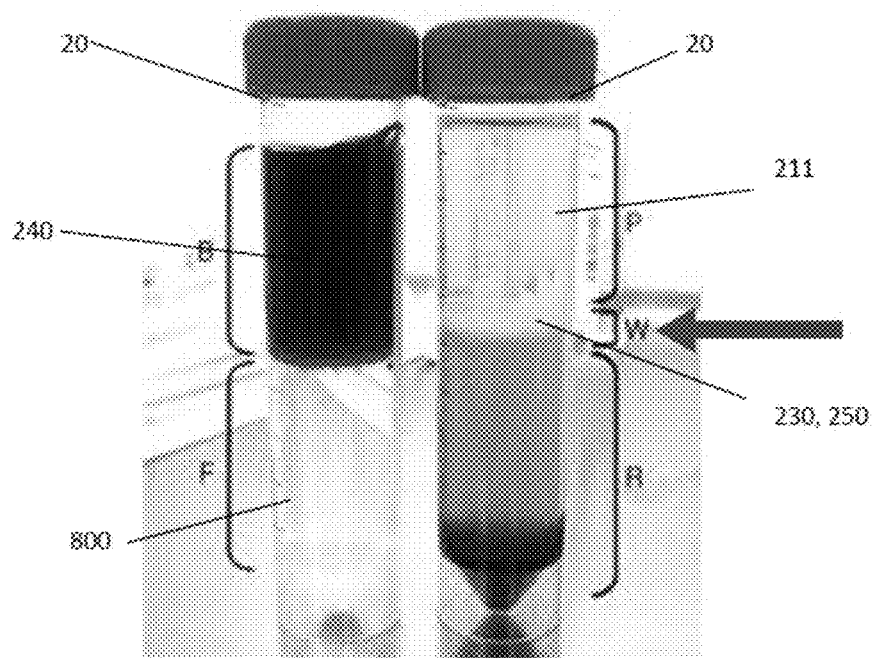
FIG. 22 shows a photograph of two 50 ml vials, the one on the left being prior to centrifuging with a sucrose gradient that is commercially available at the bottom and the material above it. The 50-ml vial on the right is after centrifuging showing the non-whole cell fraction above the interface layer.

After this, as shown in FIGS. 20 and 22, the step of separating the cells 240 from the non-whole cellular components can occur by a density centrifugation, if so desired. The whole cells 240 are in the interface and the non-whole cell components are in the supernatant above the interface. The mixture is placed in 50 ml conical tubes 20 with Ficoll 800 and undergoes a Ficoll-Paque separation under centrifugation wherein a cell density gradient is established by spinning at 400×g for 30 minutes at room temperature, preferably about 20 degrees C. The mixture includes cellular or non-cellular components or a combination thereof. All fluid 211 above the interface 230 can be removed which includes the desired non-whole cell components and which excludes the whole cells 240, 250 or all the fluid 211 and the interface 230 can be removed together.

Typically, non-whole cell fragments, or membrane components have a diameter of 40-100 nm and can be separated within a density of 1.13-1.19 g/mL in a sucrose solution, and can be sedimented by centrifugation at 100,000 g. In fact, these fragments, or cell fractions, or microvesicles, have been collectively referred to as exosomes. Ranging in size from 20-1000 nm in diameter, they have been similarly referred to as nanoparticles, microparticles, shedding microvesicles, apoptotic blebs, and human endogenous retroviral particles. There are few firm criteria distinguishing one type of microvesicle from the other.

Following removal of the cell fraction, the supernatant is further filtered through 0.45 and 0.2 μm filters. Exosomes are further collected and separated within the suspension in multiple centrifugation steps with increasing centrifugal strength to sequentially pellet cells (300 g), microvesicles (10,000 g) and ultimately exosomes (100,000 g). Cells can be deliberately removed to achieve a mixture having the non-whole cell fragments and microvesicles or can be kept forming a combination of whole cells and non-cellular components.

Subsequent separation using density gradient-based isolation, using sucrose or commercially available prep can be applied to obtain more pure exosome preparations. Recent reports encouraging the use of iodixanol-based gradients for improved separation of exosomes from viruses and small apoptotic bodies are considerations left open to be adopted or adapted in refinement. Differing from sucrose, iodixanol forms iso-osmotic solutions at all densities, thus better preserving the size of the vesicles in the gradient, and both technologies are available to best isolation technology. In addition to these traditional isolation techniques, easy-to-use precipitation solutions, such as EXOQUICK™ and TOTAL EXOSOME ISOLATION™ (TEI), that have been commercialized reduce the need for expensive equipment or technical know-how. Although their mode-of-action has not been disclosed or validated, these kits are commonly used.

Figure 23:
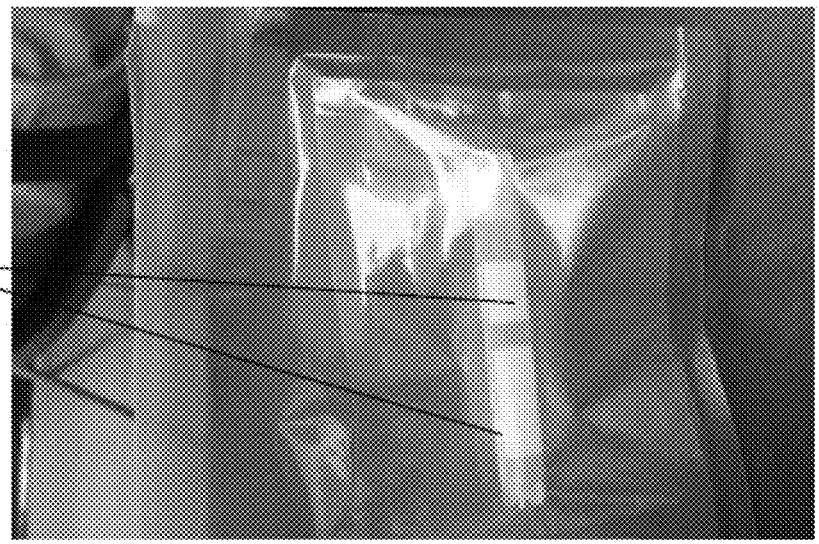
FIG. 23 is a representative photograph of the final packaging.

Once the mixture is completed, the method can include additional steps. This leads to the use of a bone blend 102 shown in FIGS. 23 and 24, preferably from the same vertebral bone or at least bone from the same donor.

When the mixture is prepared, it can have whole cells exclusively, or in combination, or even no whole cells, but will have the mechanically selected non-whole cellular components including vesicular components and active and inactive components of biological activity, cell fragments, cellular excretions, cellular derivatives, and extracellular components.

In one embodiment, the composition includes the whole cells in the mixture. In that embodiment, it is possible to provide bone particles with the mixture either in the mixture or separately to be combined at the time of use.

Figure 24:
FIG. 24 is a photograph showing the ground bone.

In one embodiment, the bone is ground to a particle size of 100-300 μm, see FIG. 24. The bone mixture has 1.5 cc of mineralized cancellous bone 104, 1.5 cc of mineralized cortical bone 105 and 2.0 cc of demineralized cortical bone 106 yielding 30 percent, 30 percent and 40 percent respectively of the total 5 cc (5 gram) of bone material 102. The ranges coincide with the 1 cc of mixture when resuspended in 3 cc of saline to provide a bone particle and mixture for implantation, which can be by packing, injection, scaffolding or any other suitable means, into a patient in a fracture healing procedure, by way of example.

Other ranges of bone particle sizes and mixture can be employed depending on the application which, in this example, was bone regeneration. Lower volumes and concentrations may be more suited for less intrusive bone repairs or more if larger if larger amounts of material are needed as in a hip defect or repair.

A cryopreservation liquid according to the invention is obtained by dissolving a polymer such as poly-lysine in physiological solutions by 1-50 w/w %; preferably by 2-20 w/w %, particularly preferably by 3-15 w/w %, and more preferably by 5-10 w/w %. The physiological solutions to be used are a physiological saline as well as culture media for culturing various cells and tissues. For example, Dulbecco-modified eagle MEM culture medium (DMEM) may be one of the preferable culture media. In place of, or in addition to poly-lysine, polyallylamines may be used. In place of these, or in addition to at least one of these, a compound(s) to be used is/are selected from other polyamines such as amino-group-introduced polysaccharides, and poly-amino acids such as poly-arginine, poly-glutamic acid and poly-aspartic acid; also a polysaccharide compound(s) that is/are selected from dextran, dextrin, pullulan and chitosan as well as polycarboxylic acid such as polyacrylic acid.

Among these polymers, preferable are polymers having a structure obtainable by polymerization of a monomer compound(s) that have both cationic and anionic substituent groups within the same monomer molecules; and especially preferable is poly-amino acids. In other words, especially preferable is a polymer having a repeating unit that has both amino and carboxyl groups. Poly-lysine to be used can be either ε-poly-L-lysine or ε-poly-D-lysine or α-poly-L-lysine. Cryoprotectant polymers have molecular weights between 100 and 100,000. The most preferable polymers fall into a group of ε-poly-L-lysine routinely used as food additives. These are either synthesized by enzymes or produced by the Streptomyces fungi and have the average molecular weights of 1000-20,000, and particularly those of 1000-10,000 with polymerization degrees ranging between 15-35, and those with 20 or lower are attempted to be produced. The average molecular weights or the average polymerization degrees are easily measurable by sodium dodecyl sulfate-polyacrylamide gel electrophoresis (SDS-PAGE), by using an electrophoresis apparatus as a means of evaluating density. Standard protein markers are used for the measurement. The poly-lysine may be heat-treated to increase its molecular weights greater than 30,000 and used as the polymer compound. However, the molecular weight range mentioned above is preferable due to the increasing viscosity with molecular weight. Because the poly-lysine having a free terminal carboxyl group has side-chain primary amino groups, their partial amidation by dicarboxylic anhydrides greatly gives excellent miscibility and solubilization performance described later. Other particularly favorable polymer compounds also adoptable according to the invention are polyallylamines with average molecular weights of 1000-1,000,000, preferably 1000-20,000. For examples, such adoptable polymers are: aqueous solution of the allylamine polymer (PAA-03 of Nitto Bosch Co., Ltd.) added with acetic anhydride or acetic acid; and the partially-methoxy-carbonylated allylamine polymer (PAA-U5000 of Nitto Bosch Co., Ltd.). The allylamine polymer, in same manner with the poly-lysine, has as side-chain groups primary amino groups only, but density of the primary amino group per unit molecular weight is larger in the allylamine polymer than in the poly-lysine. And, when the allylamine is partially carboxylated, obtained polymer compound is considered to act in same manner with partially-carboxylated poly-lysine mentioned later.

Preferably, the amino groups of the polyamine are partially blocked by being carboxylated or acetylated with carboxylic acid anhydride(s). This blockage is done by the carboxylation or acetylation of the amino groups to the degrees of preferably 50-99 mol %, particularly 50-93 mol %, more preferably 50-90 mol %, still more preferably 55-80 mol %, and the most preferably 58-76 mol %. About 50% of the amino group would be blocked by being reacted with 52-53 mol % of anhydrous carboxylic acid on basis of molar amount of the amino groups in the polyamine. In a normal reaction condition, 90-95% of the amino groups would be blocked when reacted with 100 mol % anhydrous carboxylic acid. The blocking rates above or below the above-mentioned ranges would decrease cryopreservation effects. Carboxylic acid anhydrides adoptable herein include acetic anhydride, citric anhydride, succinic anhydride, glutaric anhydride, malic anhydride, fumaric anhydride and maleic anhydride. Among these, succinic anhydride and acetic anhydride are particularly preferred.

However, polyamine with amino groups not blocked as free may also be used; thus adoptable are the degrees of carboxylation and acetylation throughout a range of 0-100 mol/mol %. In the present invention, polycarboxylic acid in which a part of the carboxyl groups is aminated may be used. More specifically, polycarboxylic acid may be partially aminated by reacting its carboxyl group with compounds such as diamine, triamine and the polyamine Adoptable diamines are ethylenediamine and hydrazides such as adipodihydrazide. Reaction of these amino compounds with carboxylic acid is by way of addition reaction with carbodiimide. In such occasion, adoptable is the degree of amination in a range of 0-100 mol/mol %. In same manner with blockage of amino groups, percentage of remaining carboxyl groups is preferably in a range of 50-99 mol %, more preferably in a range of 60-97 mol %, in each of which remaining percentage is for aminated carboxylic groups. For example, polyacrylic acid having average molecular weights of 1000-3,000,000, or 1000-10,000 in particular, is used; and 1-50 mol % of, preferably 3-40 mol % of, carboxyl groups of the polyacrylic acid are blocked with amines and carbodiimides such as ethylenediamine dihydrazide, or the like. Cryopreservation liquid according to the invention may also contain 0.3-15 w/w %, or 0.1-50 w/w % in particular, of conventional cryoprotectant materials such as DMSO, glycerol, ethylene glycol, trehalose or sucrose. Because cells are subject to damages caused by the oxidation stress during freezing and thawing, the addition of anti-oxidants to the cryoprotectant is expected to improve its preserving effects. For examples, anti-oxidants such as catalase, peroxidase, superoxide dismutase, vitamin E, vitamin C, polyphenols such as epigallocatechin gallate or glutathione may be used.

The osmotic pressure of the cryopreservation agent according to the invention is 200-1000 mOsm/kg, more preferably is 300-700 mOsm/kg, and further preferably 400-600 mOsm/kg. The cryopreservation agent according to the invention is applicable to the preservation of not only cells but also tissues. Examples of such cells and tissues to be cryopreserved by the cryopreservation agent are cultured cell lines, fertilized eggs of animal and human origin. Further examples are sperm cells, embryonic stem cells, IFS cells, mesenchymal stem cells, haemopoietic stem cells, neuronal stem cells, umbilical cord blood stem cells, hepatocytes, nerve cells, cardiomyocytes, vascular endothelial cells, vascular smooth muscle cells and blood cells. Not only animal or human cells but also plant cells can be included. Tissues and organs that are able to be preserved by the cryopreservation agent according to this invention are skins, nerves, blood vessels, cartilages, cornea, livers, kidneys, hearts and pancreatic islets.

Additional novelty of this invention is afforded in the variation in osmolality invigorated during the sublimation process. The loss of water suspends the materials in a static and transient state of relative harmony. With rehydration in the use of the product in saline, or in patient care, or in common practice of combination with other allografts, differences extant to the original formulation are extended to new metabolic demands Variations in shape and thickness and absorption will define the destiny of whole, fragment, coated, fractured, and cellular organelles.

An interesting aspect of the present invention is the ability to adjust the pH from the preferred range of 7.4 to greater or lesser amounts. This allows the electro field charge to be adjusted greater or lower as a tailored means of increasing or decreasing the predetermined time for the coating to be metabolized. Alternatively, the mixture and the protectant can be diluted prior to implantation with sterile water or saline or host blood to thin the protectant coating to shorten the time to be metabolized if so desired. In any event, the present invention insures no rinsing or separation of the protectant from the cells is required insuring much higher survivability of the donor mixture.

Current understanding advanced in this continuation is adapted to note that once frozen, the material can be thawed, sublimated through a process of cryo-lyophilization, and that various concentrations of bone marrow collections of whole cells, cell fragments, exosomes, secretome packages, and free cytokines can be produced and admixed with allograft materials.

Such collected materials are stable at temperatures above freezing, and can be further combined with synthetic and organic polymers, embedded in fibers, electrospun in fleece, adsorbed and absorbed by allografts, and used within the scope of biologic protection with minimal manipulation.

These processes can also be used to prepare a dense, bioactive derivative that can be mixed as a contribution to hydrogel cartridge technologies. Given the categorization of the polyampholyte as a hydrogel, the combination offers room temperature considerations to additive manufacturing technologies using bio inks. Printability of a biomaterial is determined by the printing technique. Although a wide range of biomaterial inks including polymers, ceramics, hydrogels and composites have been developed, the field struggles with processing these materials into self-supporting devices with tunable mechanics, degradation, and bioactivity. The development of an allograft laden hydrogel affords such potentials.

Figure 26:
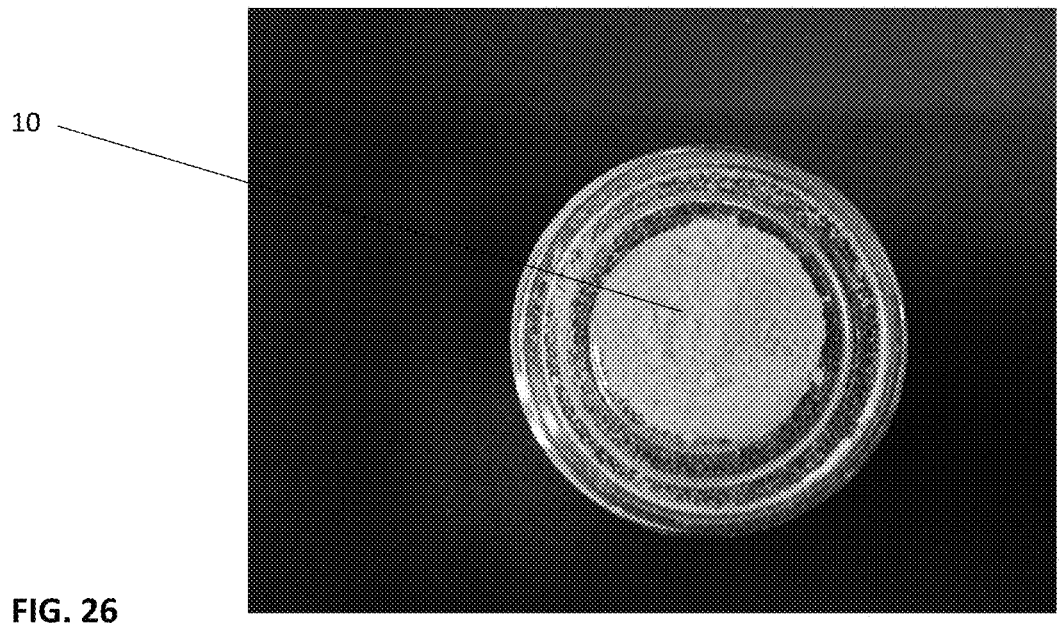
FIG. 26 is a photo of freeze-dried disc material micronized to a fine powder.
Figure 27:
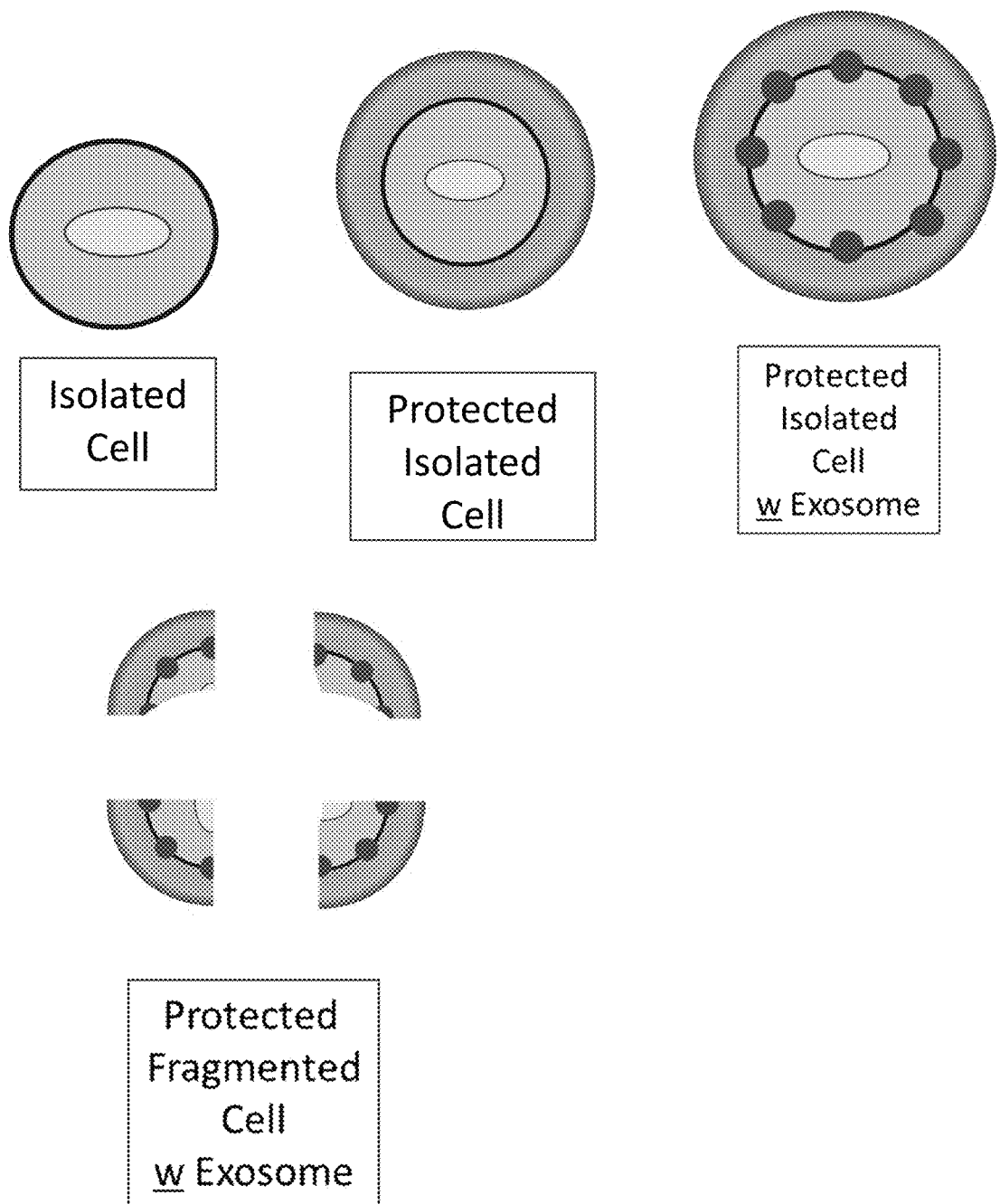
FIG. 27 is a depiction of cell Separation, Protection, Viability, Fragmentation—Fractional Coating.
Figure 28:
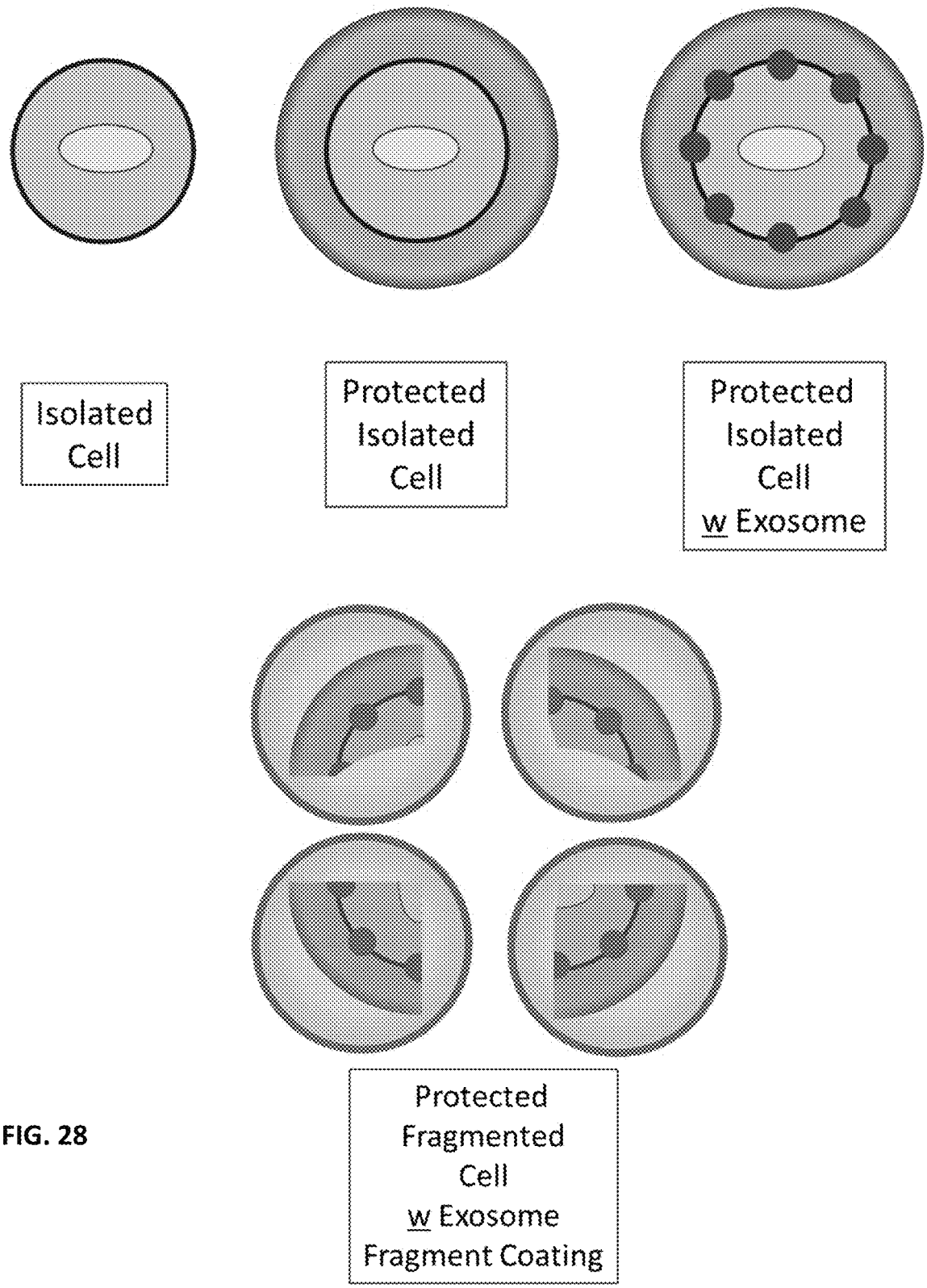
FIG. 28 is a depiction of cell Separation, Protection, Viability, Fragmentation, Fragment Full Coating during or after a Transient Thaw.

The present invention of a coated biological composition provides a novel way to replenish the disc in one embodiment. These novel disc coated compositions may be used to repair degenerative discs. There is no better source of proteoglycans than the actual disc material itself. To this end, a technique has been developed to remove the nucleus pulposus and retool the morphology of the nucleus pulposus to create a powder material that is dry and can be stored at room temperature for long periods of time. Preferably, the disc composition as shown in FIG. 26 is mixed with the mixture of biologic material and coated in a volume of the liquid protectant. This can then be reconstituted with a variety of fluids, the most suitable being normal saline or lactated ringers solution to form a flowable mixture.

The composition could also be mixed with stem cells that are derived from marrow, fat, blood, or any other source, even the interspinous ligaments. It could be combined with micronized amnion, platelet-rich plasma, and a variety of growth factors that can be encapsulated into pharmacologically active microspheres otherwise known as PAMS. The powder could also be combined with genetically altered cells that produce large amounts of glycosaminoglycans, collagen Type 1 or glucose to form the flowable mixture.

The micronized material when rehydrated has a high viscosity and allows the rehydrated material to be flowable as injectable through a cannula. This allows the rehydrated material to be stored in a syringe or other injectable device for insertion into a damaged disc to be treated.

This flowable mixture forms a composite composition between the micronized nucleus pulposus that can then be injected using a syringe or any suitable injection delivery device through a very small cannula as small as 2 mm into the disc space. This instrument can be inserted percutaneously into the disc itself during the process of discography. The flowable material of this composite composition is of a sufficiently high viscosity that once hydrated will not necessarily leak out through the injection portal or through pre-existing cracks and fissures in the annulus fibrosus. If, however, these cracks and fissures are substantial, they could be sealed with fibrin glue as part of the procedure of introducing the composites.

Figure 25:
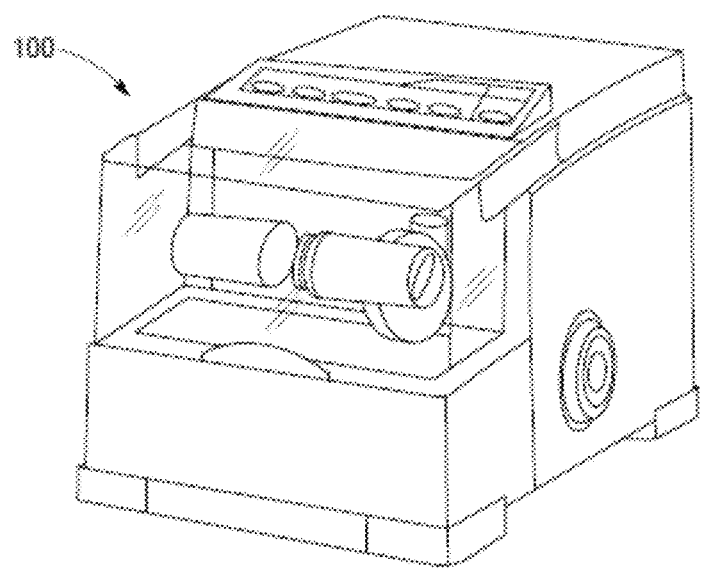
FIG. 25 is a photo of an exemplary cryomill.

The disc material is in the form of a micronized material of nucleus pulposus processed as was in US 2016/0015753 A1 filed Jul. 17, 2014, which is being incorporated by reference herein in its entirety. The actual disc material 6 is a recovered aseptically, preferably, from human cadaver spine segments from approximately T9 to L5. These are done under sterile conditions. The spinal segments are immediately transferred to a processing room where the disc is isolated by cutting the junction between the end plate and the cancellous bone maintaining intact endplates of the vertebral body above and below so as not to cause extrusion of the disc material. The endplates are then removed and the nucleus pulposus is extracted using sharp dissection. The nucleus pulposus is then aggregated from all of the intervertebral discs for that particular case and are placed in a freeze drier and or cold desiccator where the moisture is removed to under 5 percent. The freeze-dried material is then placed in aggregate into a cryomill 100, such as the one shown in FIG. 25, and micronized into a very fine powder 10 as shown in FIG. 26. Preferably, the mill 100 pulverizes the freeze-dried nucleus pulposus at low temperatures not exceeding 40° C. to prevent material degradation. The micronized material has particles sized less than 400 microns. This fine powder 10, as shown in FIG. 26, is then placed into a sterile container and can be stored under vacuum seal for long periods of time at room air. Once the fine powder material 10 is selected for administration, it is rehydrated using either normal saline, lactated ringers solution, blood, platelet rich plasma, or a combination of the above. It is then injected into the disc space using a 2-4 mm cannula, the smaller the cannula the better to prevent extrusion of the material out of the disc space following administration. Any pre-existing cracks or fissures are then sealed with fibrin glue after administration of the composite material.

This allows for a unique method of preparing the material composition of proteoglycan containing nucleus pulposus comprising the steps of: Aseptic recovery of cadaveric spine segments from T9 to L5; Removal of the discs by cutting between the cancellous bone and vertebral endplate junction; Removing the normal nucleus pulposus; Freeze drying the nucleus pulposus from multiple disc segments; Placing the freeze dried material into a cryomill 100 shown in FIG. 25; Placing the micronized disc material 10 into a sterile container for later use, shown in FIG. 26.

Additionally, a test procedure may be used to confirm viability of the material which includes the step of: mixing the micronized disc material 10 with saline, stem cells, micronized amnion, platelet rich plasma, growth factors, PAMS (pharmacologically active microspheres), genetically altered cells that produce glycosaminoglycans. This rehydrated mixture 20 can be made a flowable material suitable for delivery from a nozzle type container such as a syringe. Once this micronized powder 10 is rehydrated it can be delivered to treat damaged or degenerative disc repair.

The treatment method can include the steps of: injecting the matrix composite through a 2-4 mm cannula into the disc space. Smaller apertures through which this material may be injected may be preferable to limit extrusion of the material out of the disc space.

The spinal disc tissue can be prepared by dehydration at hypothermic temperatures.

Optionally, the disc material could be extracted from spine segments of primates or other mammals.

In accordance with another embodiment of the invention, particulate cartilage compositions for stimulating chondrogenesis and producing cartilage regeneration has particulate articular cartilage added to the biologic material prior to being coated in the volume of liquid protectant. Articular cartilage may be obtained from the articular surfaces of joints, such as from distal femurs, proximal tibias, acetabulums, heads of femurs, and/or heads of radiuses. The cartilage may be removed, for example, with a scalpel blade and is preferably removed down to subchondral bone, without removing bone. The articular cartilage for use in the present invention may include articular hyaline cartilage and/or fibrocartilage and may comprise allogeneic and/or xenogeneic cartilage.

The articular cartilage is preferably non-demineralized. Preferably, the cartilage is not subjected to harsh chemical treatments, which can alter the inherent natural properties of material within the cartilage. For example, the cartilage is preferably not subjected to demineralization treatments such as treatment with hydrochloric acid, ethylene diamine, and/or other demineralization agents. In some embodiments, the non-demineralized articular cartilage may be subjected to microbiological testing or subjected to other testing protocols that do not deleteriously alter the cartilage.

Additionally, the articular cartilage is not subjected to any physical treatments that may demineralize and/or alter the inherent natural properties of the cartilage. For example, the articular cartilage is preferably not subjected to elevated temperatures, e.g., temperatures greater than about 50° C., that may diminish the chondrogenic activity of the cartilage. However, the articular cartilage may be preserved, e.g., freeze-dried, frozen, and/or dried, after being removed from the joint. One preferred method of preserving articular cartilage is freeze-drying.

The composition includes non-demineralized cartilage particles preferably having a distribution of particle sizes. The articular cartilage particles may have sizes distributed within the range of from about 60 microns to about 500 microns, more preferably distributed in the range of from about 60 microns to about 250 microns. Some compositions, according to the present invention, may include cartilage particles having particle sizes of less than about 250 microns, i.e., cartilage powder. Some compositions may include cartilage particles having a distribution of particle sizes in the range of from about 250 microns to about 500 microns, i.e., cartilage granules. In some embodiments, the composition may comprise a combination of cartilage powder and cartilage granules.

Cartilage compositions according to the present invention may be produced by grinding non-demineralized articular cartilage to produce particles having the preferred distribution of particle sizes. The cartilage may be in the form of dry cartilage, freeze-dried cartilage, frozen cartilage, wet cartilage or mixtures thereof. In one preferred embodiment, the cartilage is freeze-dried. For example, pieces of cartilage obtained from the articular surface of one or more joints is washed in several changes of normal saline, blotted dry, and frozen rapidly, e.g., at 10° C./min or faster, in the vapor phase of liquid nitrogen (about −150° C.) or alternatively in the liquid phase of liquid nitrogen (about −196° C.). After being frozen, the cartilage is preferably rapidly placed directly on the shelves of a freeze-drying apparatus maintained at about −40° C. to about −50° C. (the condenser being cooled to from about −70° C. to about −80° C.). A vacuum level of less than about 100 millitorr is preferably maintained in the freeze-drying chamber during the freeze-drying cycle. The freeze-drying cycle may last an average of about 5 days. During the initial 30-45 minutes of the cycle, the cartilage warms from the initial frozen temperature (e.g., about −150° C.) to the temperature of the freeze-drying chamber (e.g., about −40° C.), after which it is maintained at about −40° C. for the remainder of the cycle. Preferably, the moisture content of the cartilage is reduced to from about 4 to about 5%. Over drying is preferably avoided, as this may result in the irreversible alterations of collagen and proteoglycan structures. At the end of the freeze-drying cycle, the chamber is warmed to room temperature, the vacuum released and the freeze-dried cartilage is removed.

The non-demineralized articular cartilage may be ground using any suitable grinding apparatus. For example, any grinding apparatus capable of grinding dry, hard, brittle material in seconds, such as turbo mills, disc mills, toothed disc mills, jet mills or other similar apparatuses are suitable.

Preferably, grinding is performed under conditions that preclude raising the temperature of the non-demineralized articular cartilage to a level that may diminish the chondrogenic activity of the composition. For example, grinding is preferably performed without raising the temperature of the articular cartilage above about 50° C. In some embodiments, grinding is preferably performed without raising the temperature of the cartilage above about 40° C. The temperature of the articular cartilage may be measured in any suitable manner. For example, thermocouples may be used to monitor the temperature of the cartilage directly, e.g., by measuring the temperature of the cartilage immediately after grinding, or indirectly, e.g., by measuring the temperature of the metal in the grinding mill. Continuous grinding in conventional grinding mills for 3-5 minutes can raise the temperature of the material to 70° C. or above. However, operating a grinding mill intermittently may preclude an undesirable rise in temperature. In one embodiment, freeze-dried pieces of cartilage, 1-4 mm in size, may be ground in a grinding mill operating intermittently for 20-30 second intervals.

After each grinding cycle, the cartilage may be sieved. The cartilage may be sieved through sieves of 100 to 500 microns. Sieving may be used to separate cartilage into cartilage powder (i.e., particle sizes of less than 250 microns) and cartilage granules (i.e., particle sizes of 250 to 500 microns). Grinding may be repeated until the desired distribution of particles sizes is obtained.

The present invention also provides a method for regenerating articular cartilage. Therapeutically effective amounts of cartilage composition comprising non-demineralized articular cartilage having particle sizes distributed within the range of from about 60 microns to about 500 microns may be administered at the site of a cartilage defect. The cartilage composition may be implanted at the articular surface and packed into the defect. Advantageously, in some embodiments, the cartilage composition may be packed into the defect with the use of an overlying cover.

Without wishing to be bound to any theory, it is believed that compositions, according to the invention, including non-demineralized particulate cartilage, release cartilage growth factor(s) or other substances that induce regeneration of articular cartilage. The three-dimensional shape of the particles and multiple surfaces, as well as the inventive particle sizes and distributions, enhance diffusion of the cartilage growth factor(s) or other substances from the particles. Furthermore, the absence of harsh chemical treatments and avoidance of elevated temperatures during processing facilitates the production of particles having high chondrogenic activity when mixed with the biologic material and coated with the liquid protectant with the coated biologic mixture.

Figure 29:
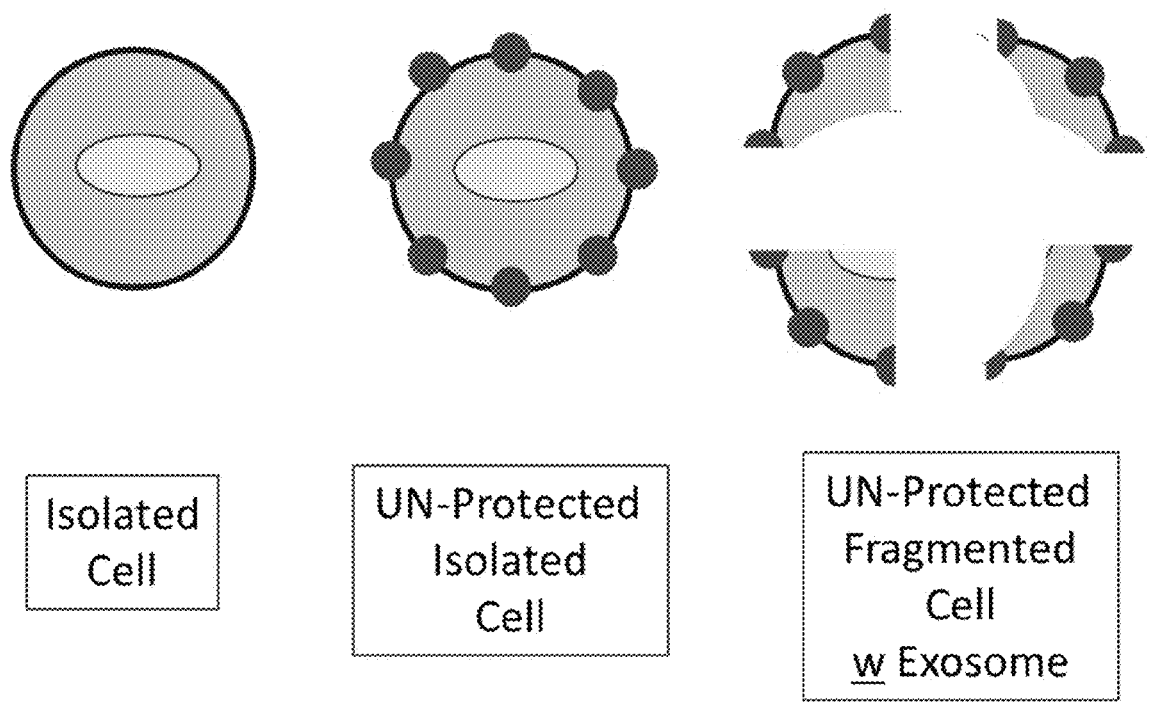
FIG. 29 is a depiction of cells Separated, Non-Protected but with BioActive, BioAvailable Fragments.
Figure 30:
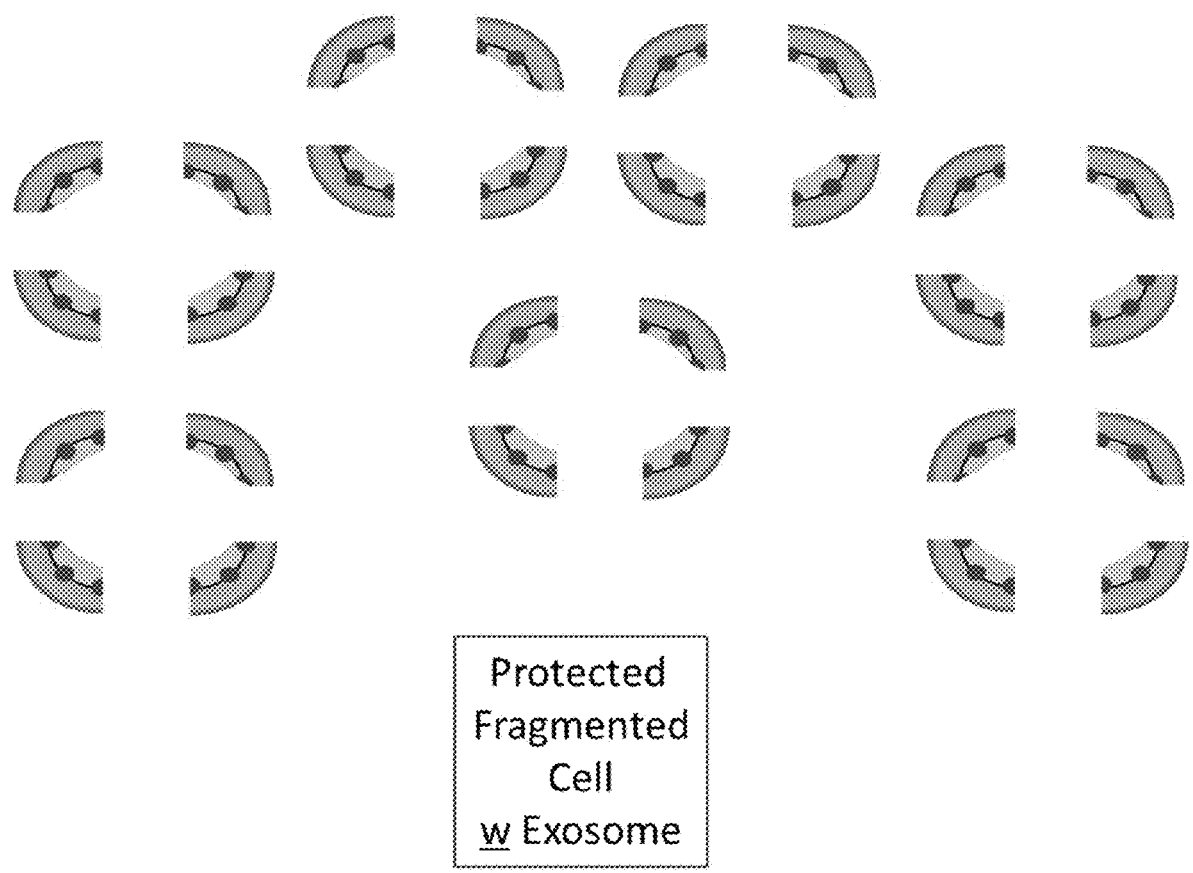
FIG. 30 is a depiction of Protected, Non-Viable Fragments but maintaining BioActive, BioAvailable Assets.
Figure 31:
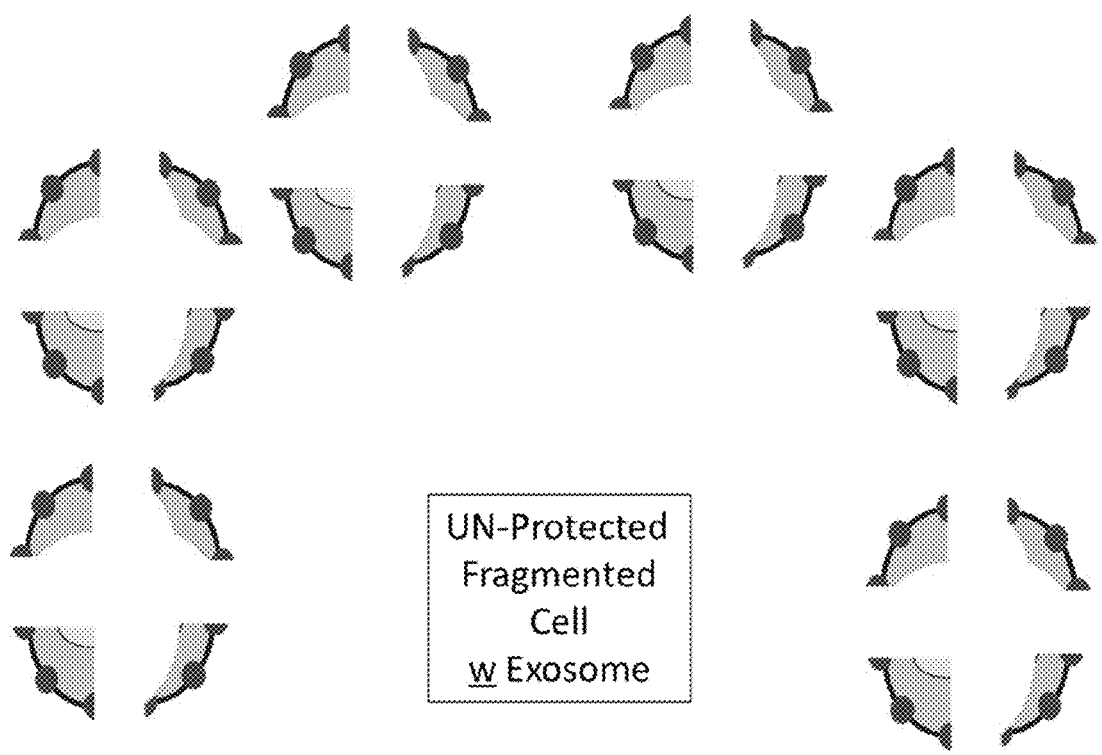
FIG. 31 is a depiction of UN-Protected, Non-Viable cells but maintaining BioActive, BioAvailable Assets.
Figure 32:
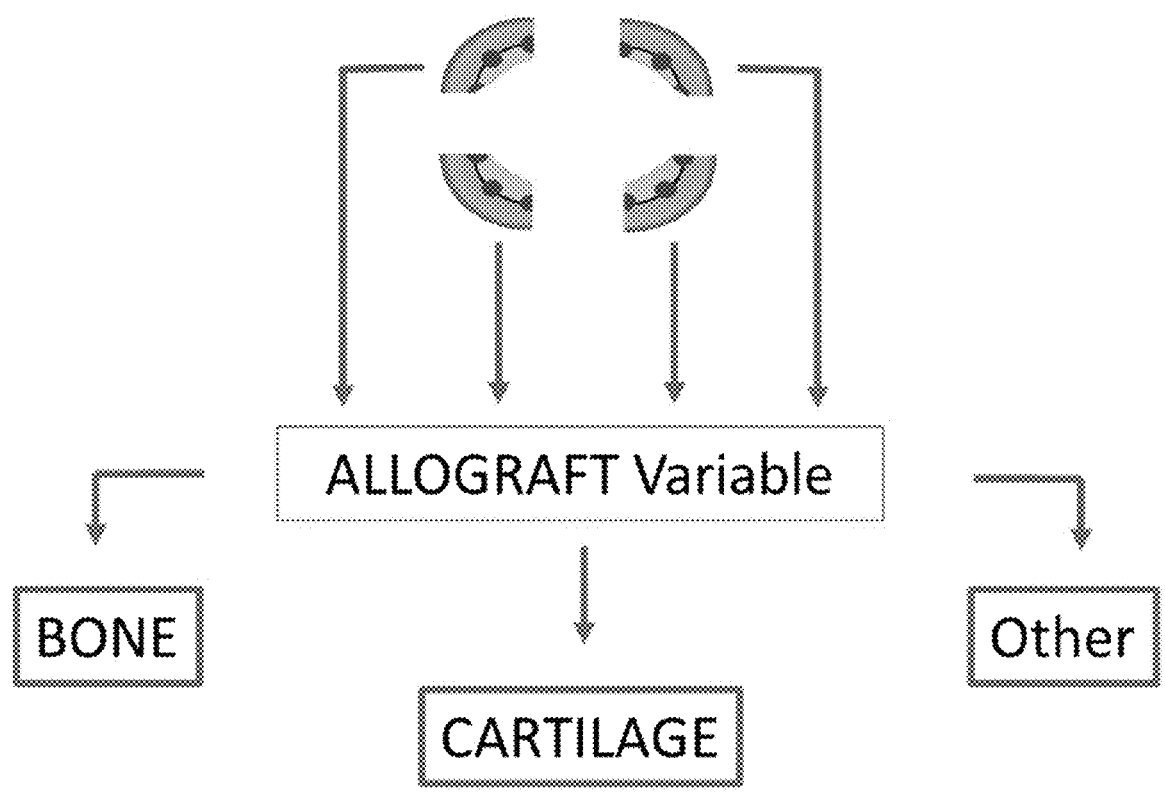
FIG. 32 is a depiction of a BioActive, BioAvailable, Protectant-Coated Fragments—Incomplete coated protected fragmented cell with exosomes and possible combinations for allograft.
Figure 33:
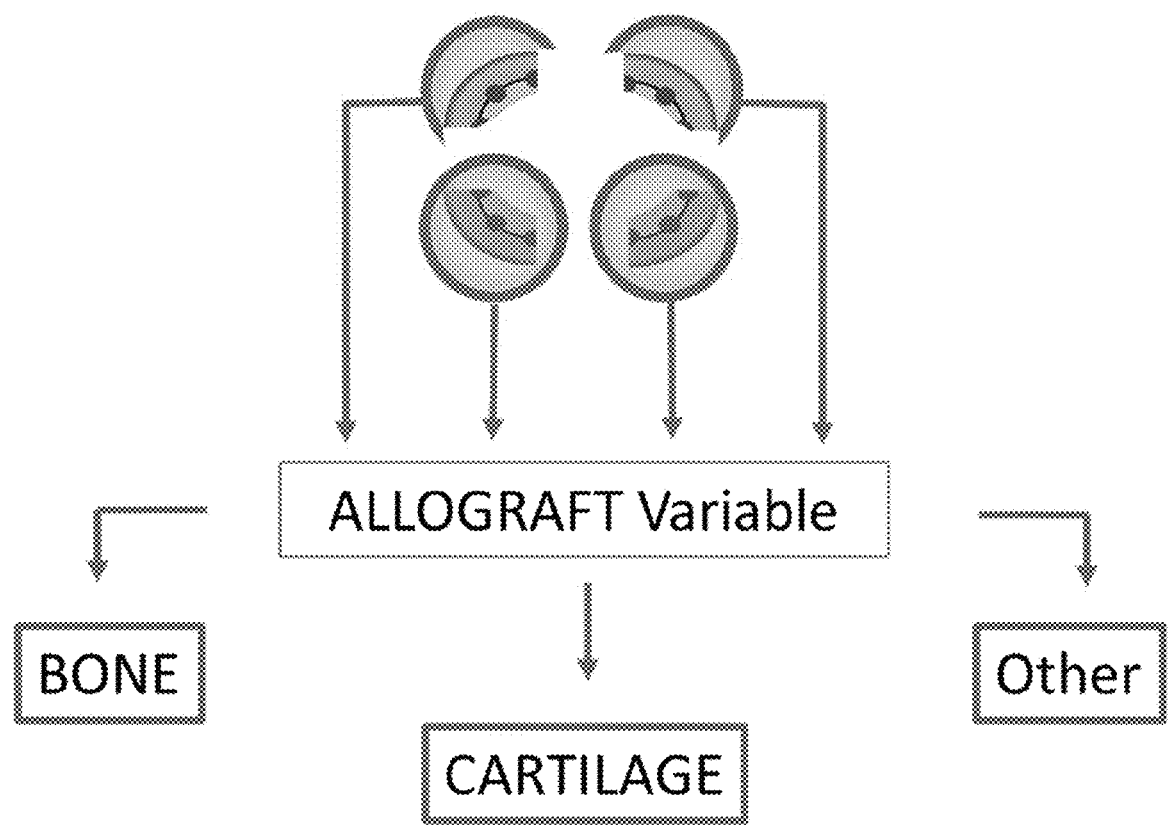
FIG. 33 is a depiction of BioActive, BioAvailable, Protectant-Coated Fragments—Incomplete and Complete coated and possible combinations for allograft.
Figure 34:
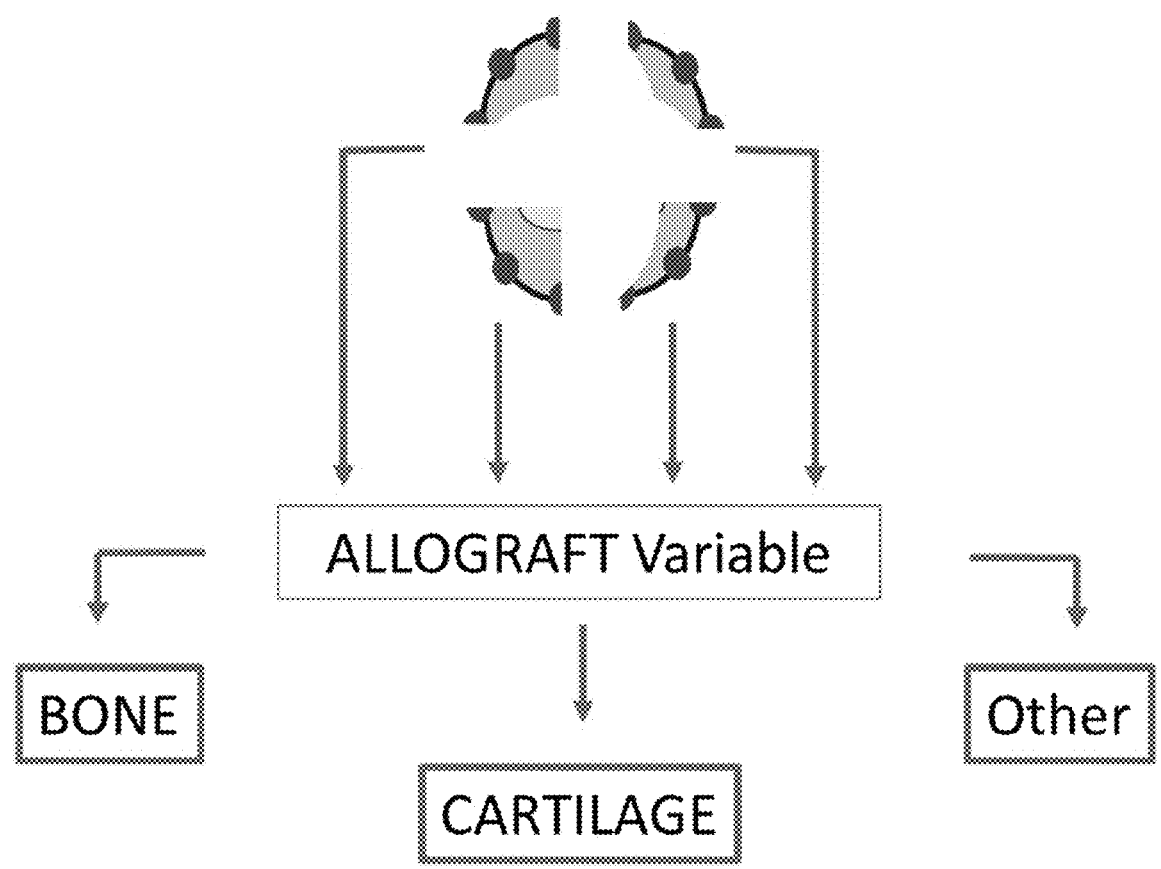
FIG. 34 is a depiction of BioActive, BioAvailable, UN-protected Fragments un-protected fragmented cell with exosomes and possible combinations for allograft.

Un-protected cells and fragments are shown in FIGS. 29, 31 and 34.

In summary, Viable Allografts represent a positive regenerative therapeutic strategy, Cells and cell fragments can be protected, as shown in FIGS. 27, 28, 30, 32 and 33, with liquid protectants such as, but not limited to polyampholyte membrane protectants, Retain cell viability, Preserve pluripotential nature of thawed tissue cells, Buffer inflammation with protective coating, Affect positive attachment bias to coating, Reduce early and ineffective differentiation, Protect from immune rejection, Eliminate early host sensitization, Provide Positive attachment for host cells to donor cells, Facilitate Cytokine and Exosome Exchange. Cryoprotectant need only be a protection during freezing, Freezing constitutes a process point and not a period of time. Cell viability is a transient, non-fixed stage biology. Cell death comports benefits to adjacent tissue regions, and to systemic signaling. Cell fragmentation, ligand shedding, exosome expulsion, and membrane elicitation are processed that afford cues to core biologic processes. Signaling while sourced as intercellular communication occurs independent of cells. Coated cells retained coated fragments that are similarly providing new and predictable functional graft foundations, depicted in FIG. 33. Other cryopreservatives can be toxic to cell but facilitate exosome and cytokine shedding. Cell Protection includes protecting BioActive, BioAvailable potentials in addition to Viability. Whole cell preservation offers a complete supplemental source of viability. Non-whole cell fragmentation, exosome, and cell cytokine release accentuate regenerative biologic activity. Both whole cell and non-whole cell biologics are essential assets to regenerative therapeutic strategies. A preferred combination of polyampholyte cryoprotectants envelop cell and fragments and promote and provide an enhanced surface area for both host and donor cell attachment. Other biochemical combinations that have been used in cell preservation may also demonstrate retention of BioActive and BioAvailable attributes. These attributes separate from Viability are claimed in context of non-whole cell fragment—allograft products. Each of the UN-protected by liquid protectant methods will contain cell fragments that are recovered by the processes described in U.S. Pat. No. 9,687,511 by Weston et al. Cell compositions in their respective formulations intended for cryoprotection may be frozen and thawed, refrozen and cryo-lyophilized to reduce the fluid volume, concentrate the cytokine, eliminate the cellular component, and enrich the concentration of the viable component of the tissue to be considered a distinct distillate of marrow components but of other organ cell sources as well. Lyophilized materials may be recombined with allografts of bone, cartilage, disc and skin in example, but a reasonable extension would include other tissues similarly prepared (liver lyophilized, and reperfused with bone marrow distillate, etc.). Bone marrow fragmented cell exudates, both with Viable Cells and additionally augmented with BioActive and BioAvailable Cytokines could be mixed with allograft before cryo-lyophilization. The intended strategy is to comport biologic activity, both with and without viable cell count, and to freeze the potential as a cryo-lyophilized material rather than to require long-term freezing of intact and whole cells.

The present invention, when processed to make a coated biological composition suspended in a liquid protectant frozen and then either freeze-dried or hypothermically dried, reduces the overall moisture content to approximately 5%. While this increases the concentration levels of the biologic material, it also dramatically reduces the volume of the liquid protectant to such a level that the dried coated biological composition, when micronized into particles of 1000 microns or less, can be stored at ambient conditions and, when rehydrated with a suitable liquid such as normal saline or whole blood is suitable for direct implantation without requiring decanting or washing of the hydrated composition.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A method of making a coated biological composition comprising the steps of:
   (a) grinding a cut vertebral body to produce a mixture comprising crushed vertebral bone and bone marrow, wherein the cut vertebral body is obtained from a cadaver donor;
   (b) mechanically separating cellular and non-cellular components of the bone marrow from the vertebral bone in the mixture by tumbling and sieving the vertebral bone from a decanted fluid of the bone marrow comprising the cellular components comprising whole cells, and non-whole cellular components comprising non-whole cell components;
   (c) concentrating the decanted fluid by centrifugation;
   (d) filtering the decanted fluid through a blood filter to form a mixture including the cellular and non-whole cellular components and remove any remaining vertebral bone;
   (e) separating the cellular components comprising whole cells and non-whole cellular components of the bone marrow directly from the mixture of step (d) by density gradient centrifugation, wherein the separation under centrifugation establishes a cell density gradient;
   (e) collecting non-cellular fractions or non-cellular components or combinations-thereof of predetermined density from the gradient;
   (f) washing the non-cellular fractions or non-cellular components or combinations thereof to create a mixture;
   (g) suspending the mixture of step (f) to a predetermined concentration in a liquid protectant to form the coated biological composition;

(h) freezing the coated biological composition at a predetermined controlled rate; and
   (i) thawing and freezing the coated biological composition a second time prior to storage;
   (ii) thawing and refrigerating the coated biological composition;
   (iii) thawing and concentrating the coated biological composition by drying; or
   (iv) lyophilizing the frozen coated biological composition for ambient or room temperature storage.

2. The method of claim 1, wherein the liquid protectant is a polyampholyte protectant or polyampholyte cryoprotectant, a glycerol-based protectant, dimethyl sulfoxide (DMSO), a glycol, trehalose, a molecular hydrogel preservative, sucrose or a dextrose based protectant.

3. The method of claim 1, further comprising adding a volume of cartilage particles, wherein the particles are intermixed with the coated biological composition and coated with the liquid protectant.

4. The method of claim 1, further comprising adding a volume of nucleus pulposus particles, wherein the particles are intermixed with the coated biological composition and coated with the liquid protectant.

5. The method of claim 1, further comprising adding a volume of bone particles, wherein the particles are intermixed with the coated biological composition and coated with the liquid protectant.

6. The method of claim 5 wherein the coated biological composition is freeze dried or hypothermic dehydrated.

7. The method of claim 6 wherein the dried coated biological composition is micronized into particles of 1000 microns or less.

8. The method of claim 6 wherein the dried coated biological composition is micronized into particles of 400 microns or less.

9. The method of claim 5 wherein the bone particles include a mixture of cortical bone particles and cancellous bone particles.

10. The method of claim 1, further comprising:
   diluting the coated biological composition in saline without spinning;
   and implanting the diluted mixture by packing, injection, or any other suitable means into a patient.

11. The method of claim 10 wherein the step of diluting the mixture includes warming the mixture at a temperature of 37 degrees C. for 2 to 3 minutes in a warm water bath.

12. The method of claim 1 wherein the thawed coated biological composition is re-frozen for storage prior to use.

13. The method of claim 1 wherein the thawed coated biological composition is refrigerated above freezing for storage prior to use.

14. The method of claim 1 wherein the thawed coated composition is processed to be stored at room temperature for storage.

15. The method of claim 1 wherein the thawed coated biological composition is concentrated by drying prior to being stored at room temperature to form a dried coated biological composition.

16. The method of claim 15 wherein the dried coated biological composition has a moisture content of 5% or less.

17. The method of claim 16 wherein an initial volume of the liquid protectant when reduced to a solid for drying or freeze-drying yields 5% or less of the initial volume.

18. The method of claim 17 wherein the dried coated biological composition when reconstituted in a liquid is suitable for direct implantation.

19. The method of claim 17 wherein the liquid protectant is a cryoprotectant.

20. The method of claim 1 wherein the liquid protectant is a polyampholyte protectant or polyampholyte cryoprotectant.

21. The method of claim 1 wherein the liquid protectant is dimethyl sulfoxide (DMSO).

22. The method of claim 1, further comprising:
   collecting whole cells from the cellular components of the bone marrow; and
   adding the whole cells to the mixture suspended in the liquid protectant, wherein the liquid protectant coats the whole cells, and the coating deters attachment of the whole cells to the non-cellular fractions or non-cellular components or combinations thereof for a predetermined time.

23. The method of claim 22 wherein the coating retards or reduces premature differentiation of the whole cells of the mixture.

24. The method of claim 22 wherein the coating forms a spherical shrouding shell about each whole cell.

25. The method of claim 1, wherein the coating buffers inflammation in a subject after implantation of the coated biological composition.

26. The method of claim 1 wherein the coating sustains regenerative potential and biologic function of the mixture during preservation and implantation.

27. The method of claim 1 further comprising:
   implanting the coated biological composition in a patient; wherein the coating forms a shell which is configured to be metabolized by host cells of the patient after implantation after a predetermined time of three or more days.

28. The method of claim 27 wherein the predetermined time is up to six days.

29. The method of claim 1 wherein the non-cellular components derived from bone marrow further includes a select number of non-whole cell fractions including one or more of exosomes, transcriptosomes, proteasomes, membrane rafts, and lipid rafts.

30. The method of claim 29, further comprising:
   implanting the coated biological composition in a patient having host cells; wherein
   the combination of non-whole cell components with a select number of the non-whole cell fractions sustains pluripotency in the host cells.

31. The method of claim 30 wherein the select number of the non-whole cell fractions sustains pluripotency in the host cells including differentiated committed cells and non-differentiated and non-committed cells.

32. The method of claim 1 wherein the biological composition extends regenerative resonance that compliments or mimics tissue complexity.

33. The method of claim 1, wherein the protectant creates a physical, electrical, or chemical gradient or combination thereof for tissue regeneration.

34. The method of claim 1, wherein the step of freezing the suspended mixture at a predetermined controlled rate or freezing the coated biological composition a second time comprises cryopreservation of the mixture.

35. The method of claim 34 wherein the composition is maintained at ambient temperature prior to freeze drying.

36. The method of claim 34, wherein cryopreservation occurs at a temperature that is sub-freezing.

37. The method of claim 36 wherein the cryopreservation temperature is from 0 degrees C. to −200 degrees C.

38. The method of claim 1 wherein the mixture of step (f) includes organelle fragments.

39. The method of claim 1, wherein the mixture of step (f) is intermixed with a liquid protectant of a polyampholyte protectant for direct implantation, wherein said protectant is a 1-50 w/w % aqueous solution of at least one polyamine polymer compound comprising at least one polymer of units having side-chain amino groups, said at least one polymer of units being selected from a group consisting of ε-poly-L-lysine, a-poly-L-lysine, a poly-arginine, an allylamine polymer, and a partially methoxy-carbonylated allylamine polymer.

40. The method of claim 39, wherein said liquid protectant is obtained by dissolving the at least one polyamine polymer compound in a physiological solution.

41. The method of claim 39, wherein the physiological solution is a saline, Dulbecco-modified eagle MEM culture medium (DMEM), or a culture medium for cells or tissues.

42. The method of claim 39, wherein said at least one polymer compound is €-poly-L-lysine having number-average molecular weight in a range of 1000-20,000.

43. The method of claim 39, wherein remaining side-chain amino groups or remaining side-chain and terminal amino groups of the at least one polymer compound are not blocked by covalent bonding.

* * * * *